United States Patent
Kaufman-Janette et al.

(10) Patent No.: US 10,076,558 B2
(45) Date of Patent: Sep. 18, 2018

(54) PROPHYLACTIC NORMALIZATION OF CUTANEOUS WOUND REPAIR

(71) Applicant: RNW SKN, LLC, Coral Gables, FL (US)

(72) Inventors: Joely Kaufman-Janette, Coral Gables, FL (US); Alejandro Cazzaniga, Coral Gables, FL (US)

(73) Assignee: RNW SKN, LLC, Coral Gables, FL (US)

( * ) Notice: Subject to any disclaimer, the term of this patent is extended or adjusted under 35 U.S.C. 154(b) by 0 days.

(21) Appl. No.: 15/119,644

(22) PCT Filed: Feb. 18, 2015

(86) PCT No.: PCT/US2015/000028
§ 371 (c)(1),
(2) Date: Aug. 17, 2016

(87) PCT Pub. No.: WO2015/126527
PCT Pub. Date: Aug. 27, 2015

(65) Prior Publication Data
US 2017/0056484 A1 Mar. 2, 2017

Related U.S. Application Data

(60) Provisional application No. 61/941,112, filed on Feb. 18, 2014.

(51) Int. Cl.
| | |
|---|---|
| *A61K 38/48* | (2006.01) |
| *A61K 8/66* | (2006.01) |
| *A61K 9/00* | (2006.01) |
| *A61K 45/06* | (2006.01) |
| *A61K 35/16* | (2015.01) |
| *A61Q 19/08* | (2006.01) |

(52) U.S. Cl.
CPC .......... *A61K 38/4893* (2013.01); *A61K 8/66* (2013.01); *A61K 9/0014* (2013.01); *A61K 9/0019* (2013.01); *A61K 9/0021* (2013.01); *A61K 35/16* (2013.01); *A61K 45/06* (2013.01); *A61Q 19/08* (2013.01); *C12Y 304/24069* (2013.01)

(58) Field of Classification Search
CPC .......... A61K 38/4893; A61K 9/0021; A61K 9/0014; A61K 9/0019; C12Y 304/24069; A61Q 19/09
See application file for complete search history.

(56) References Cited

U.S. PATENT DOCUMENTS

| | | | |
|---|---|---|---|
| 6,447,787 B1 * | 9/2002 | Gassner | A61K 31/335 424/236.1 |
| 2006/0051377 A1 | 3/2006 | First | |

FOREIGN PATENT DOCUMENTS

WO 2006035225 A1 4/2006

OTHER PUBLICATIONS

Wilson A.D. "Eradication of keloids: Surgical excision followed by a single injection of intralesional 5-fluorouracil and botulinum toxin". Can J Plast Surg., 2013, vol. 21, No. 2, pp. 87-91.*
Eliza Drewa. "Facial rejuvenation can come from diluted botulinum toxin injections". The Aesthetic Channel e-Newsletter, Dec. 1, 2011, pp. 1-4; retrieved on Jun. 21, 2017 from http://aestheticchannel.modernmedicine.com/cosmetic-surgery-times/news/modernmedicine/modernmedicine-feature-articles/facial-rejuvenation-can-?page=full.*
Sherris D A et al: "Botulinum Toxin to Minimize Facial Scarring", Facial Plastic Surgery, Thieme Medical Publishers, Stuttgart, DE, vol. 18, No. 1, Feb. 1, 2002 (Feb. 1, 2002), pp. 35-39, XP009050233.
Xiao Zhibo et al: "Effects of botulinum toxin type a on collagen deposition in hypertrophic scars.", Molecules (Basel, Switzerland) 2012, vol. 17, No. 2, Feb. 2012, pp. 2169-2177, XP002738555.
Ziade Makram et al: "Use of botulinum toxin type A to improve treatment of facial wounds: a prospective randomised study", Journal of Plastic, Reconstructive & Aesthetic Surgery : JPRAS Feb. 2013, vol. 66, No. 2, Feb. 2013 (Feb. 2013), pp. 209-214, XP002738556.
Gassner H G et al: "Treatment of Facial Wounds With Botulinum Toxin A Improves Cosmetic Outcome in Primates", Plastic and Reconstructive Surgery, Wolters Kluwer Health, US, vol. 105, No. 6, May 1, 2000 (May 1, 2000), pp. 1948-1955, XP009050221.
Zhibo X et al: "Botulinum toxin type affects cell cycle distribution of fibroblasts derived from hypertrophic scar", Journal of Plastic, Reconstructive and Aesthetic Surgery, Churchill Livingstone, GB, vol. 31, No. 9, Sep. 1, 2008 (Sep. 1, 2008), pp. 1128-1129, XP024518587.
Zhibo Xiao et al: "Botulinum Toxin Type A Inhibits Connective Tissue Growth Factor Expression in Fibroblasts Derived From Hypertrophic Scar", Aesthetic Plastic Surgery, Springer-Verlag, NE, vol. 35, No. 5, Apr. 1, 2011 (Apr. 1, 2011), pp. 802-807, XP019963685.
International Search Report for Application No. PCT/US2015/000028 dated May 8, 2015.

* cited by examiner

*Primary Examiner* — Vera Afremova
(74) *Attorney, Agent, or Firm* — Lerner, David, Littenberg, Krumholz & Mentlik, LLP

(57) ABSTRACT

The present invention relates to methods of inhibiting scar formation in a skin wound as well as methods of promoting tissue regeneration in a skin wound in a subject in need thereof comprising administering in or near said wound an effective amount of one or more neurotoxins.

23 Claims, 12 Drawing Sheets

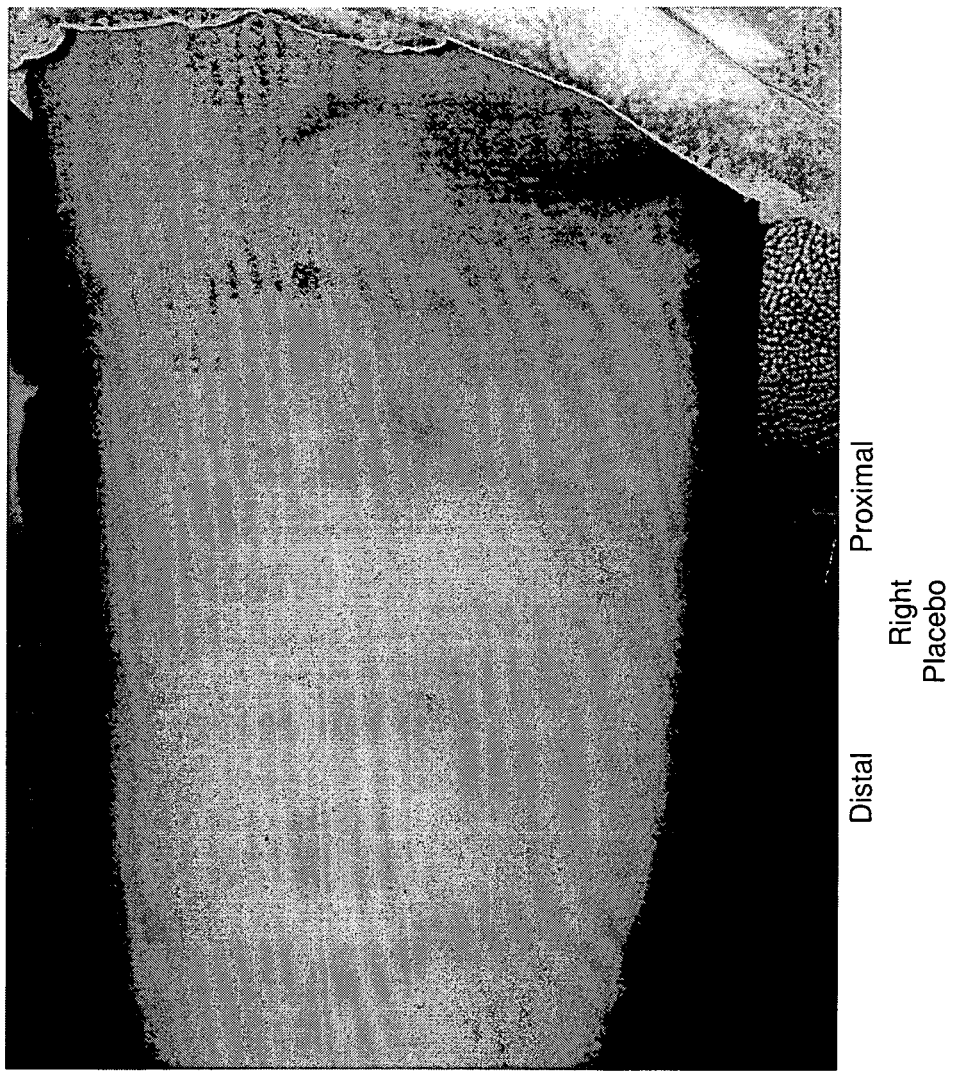
FIGURE 1: Photographs of wound sites at 120 days post-wounding for Subject 3
SUBJECT 003

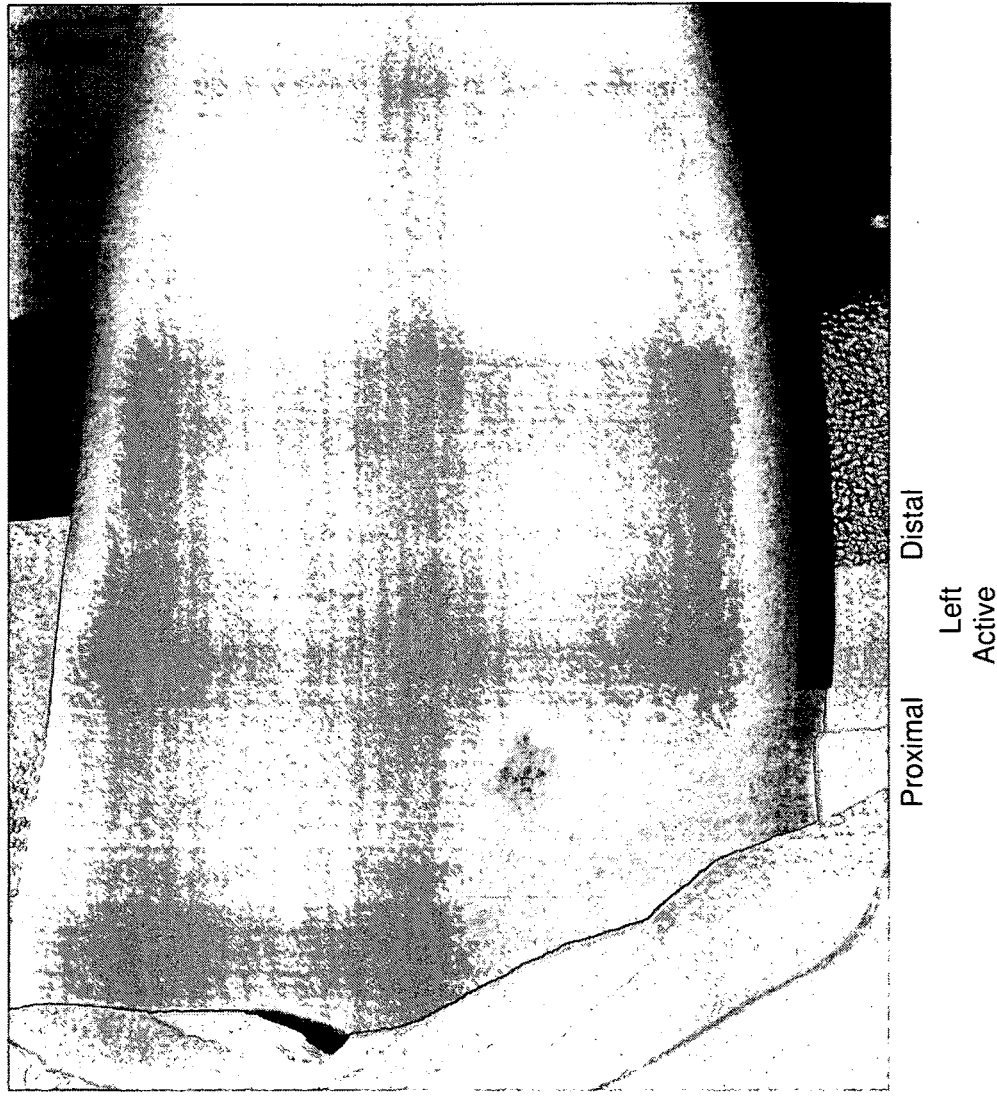
FIGURE 1 (continued): Photographs of wound sites at 120 days post-wounding for Subject 3 SUBJECT 003

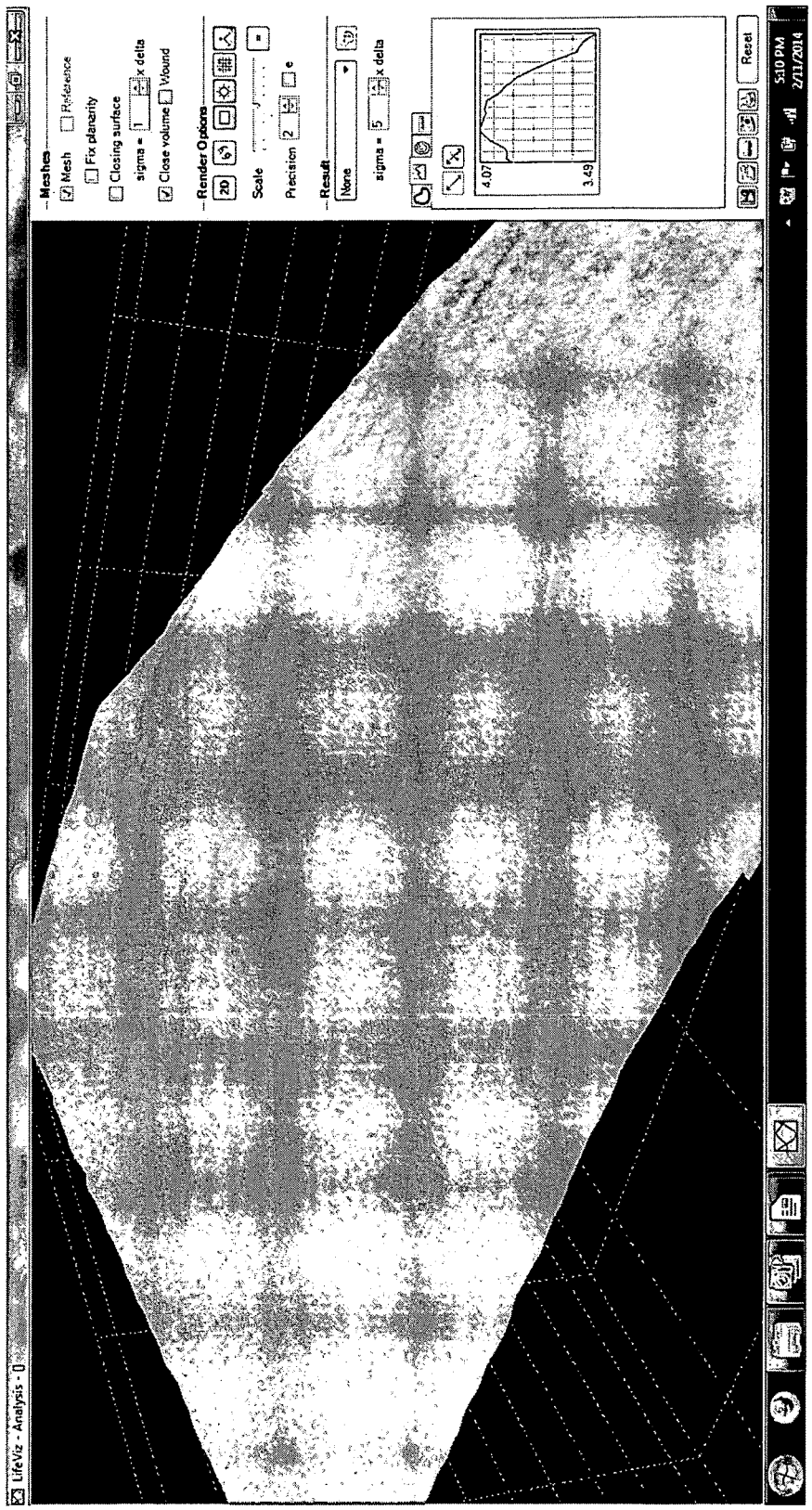
FIGURE 2: Left (BTXA) Distal 3-dimensional image 120 days post-wounding for Subject 3
SUBJECT 003
Left Distal 3D Image

FIGURE 2 (continued): Left (BTXA) Distal 3-dimensional image 120 days post-wounding for Subject 3
SUBJECT 003
Left Distal 3D Image

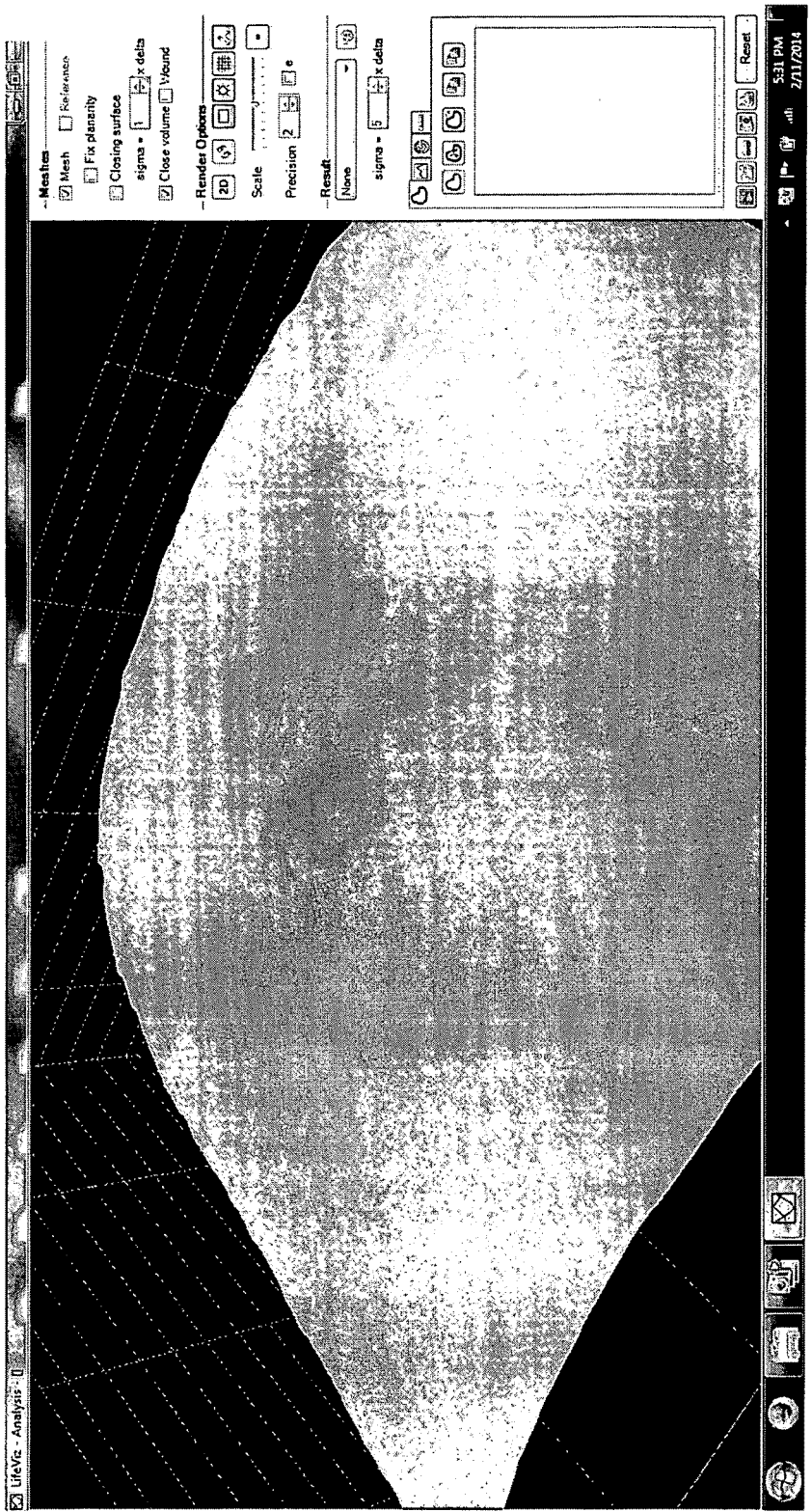
FIGURE 3: Right (Placebo) Distal 3-dimensional image 120 days post-wounding for Subject 3
SUBJECT 003
Right Distal 3D Image

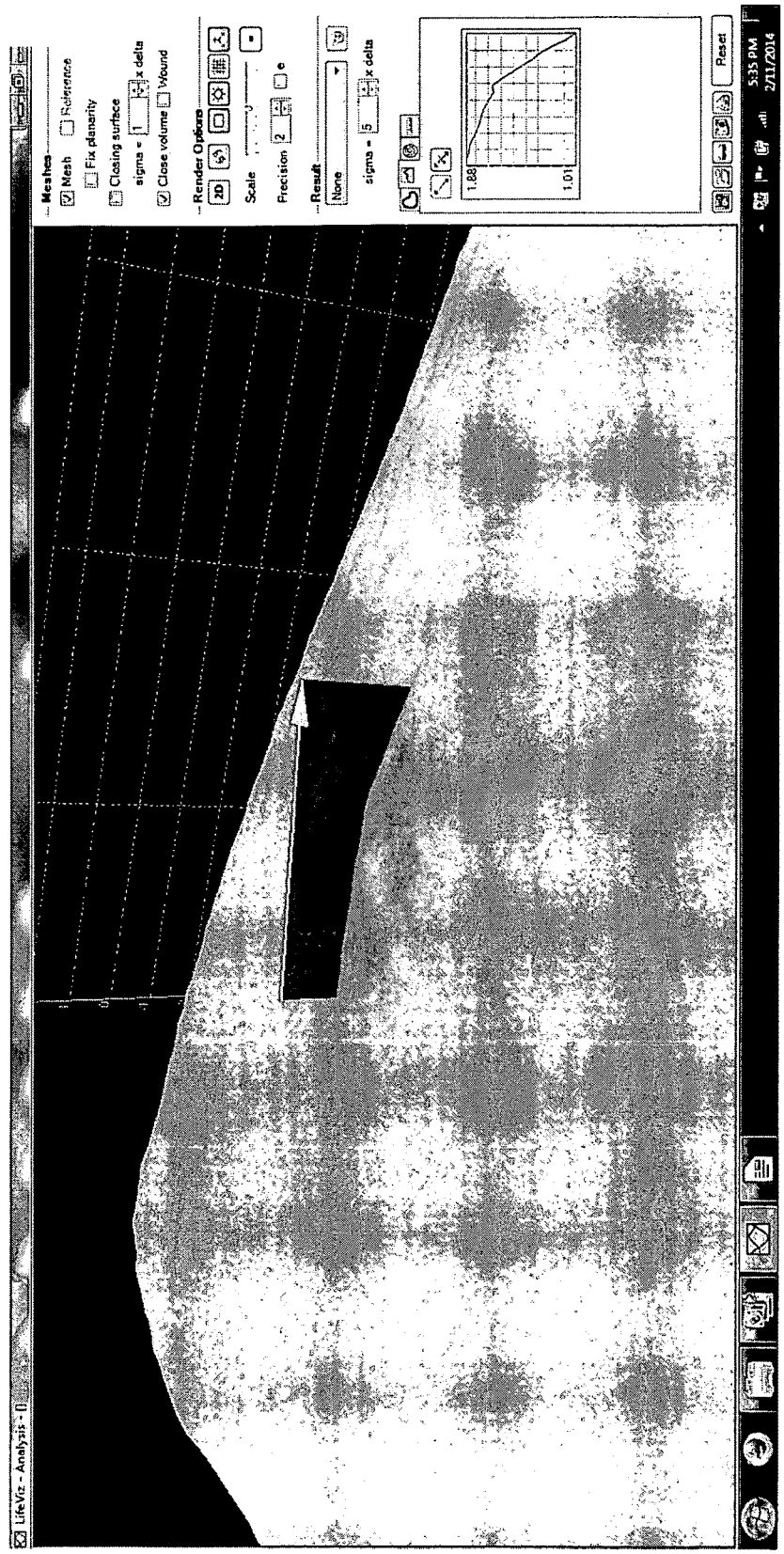
FIGURE 3 (continued): Right (Placebo) Distal 3-dimensional image 120 days post-wounding for Subject 3
SUBJECT 003
Right Distal 3D Image

FIGURE 4: Histology samples stained with Peroxidase 120 days post-wounding for Subject 3
SUBJECT 003
TGFβ1 Stained with Peroxidase (appears as red)
Day 120 Right Full Section
Placebo (a lot more red stain)

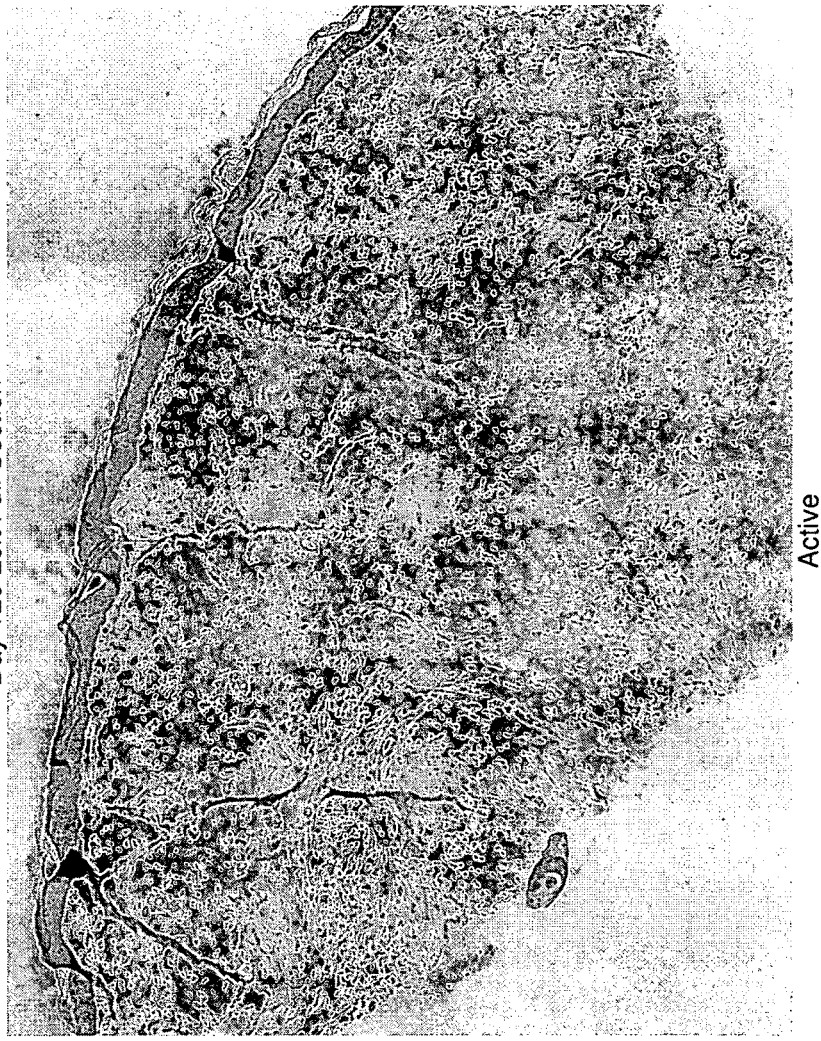
FIGURE 4 (continued): Histology samples stained with Peroxidase 120 days post-wounding for Subject 3
SUBJECT 003
TGFβ1 Stained with Peroxidase (appears as red)
Day 120 Left Full Section
Active

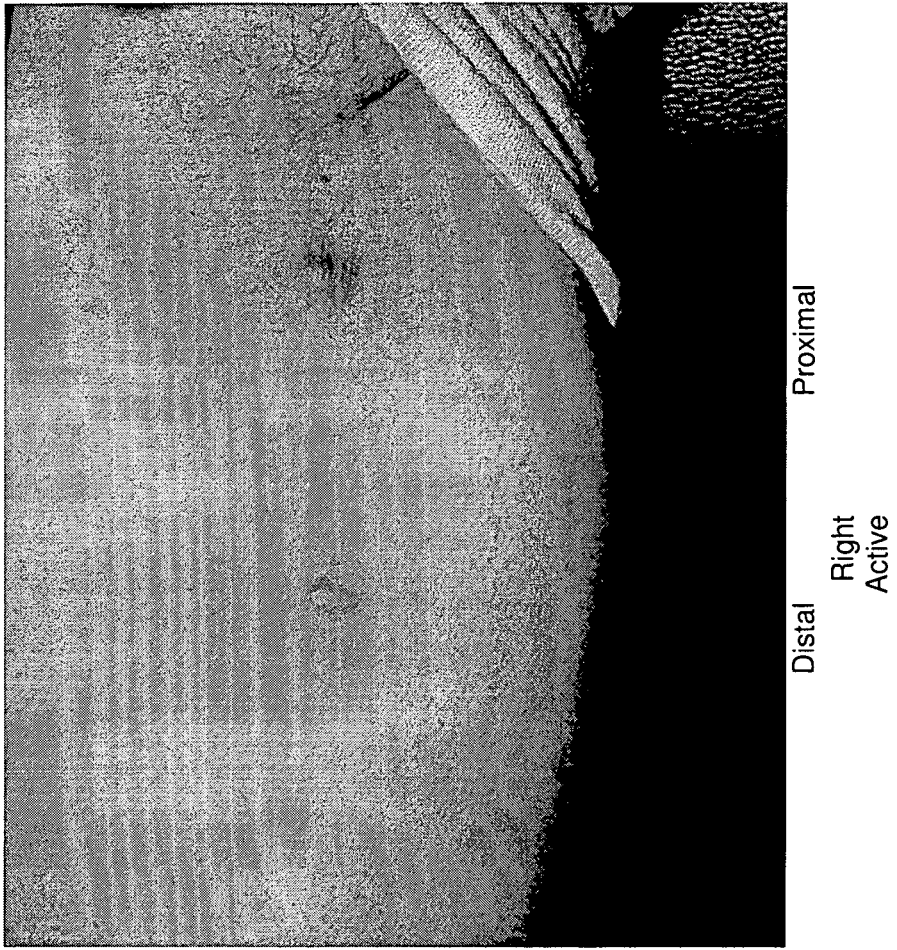
FIGURE 5: Photographs of wound sites at 120 days post-wounding for Subject 6

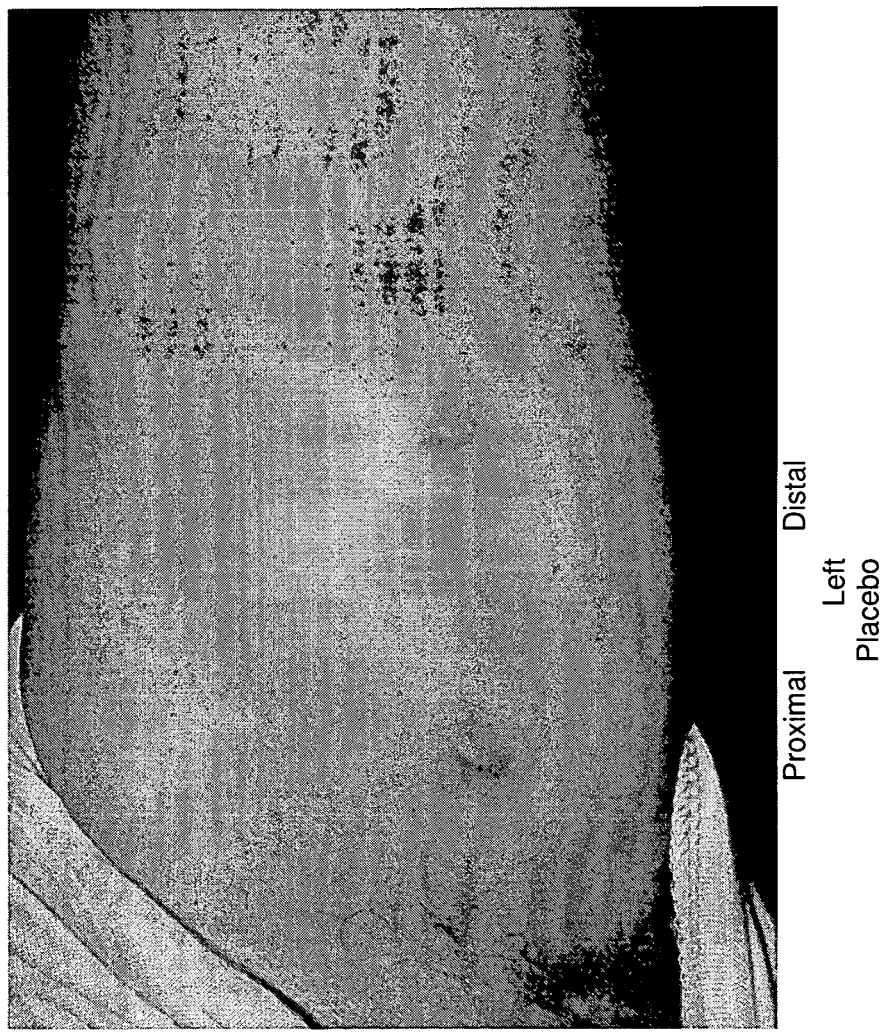
FIGURE 5 (continued): Photographs of wound sites at 120 days post-wounding for Subject 6
SUBJECT 006

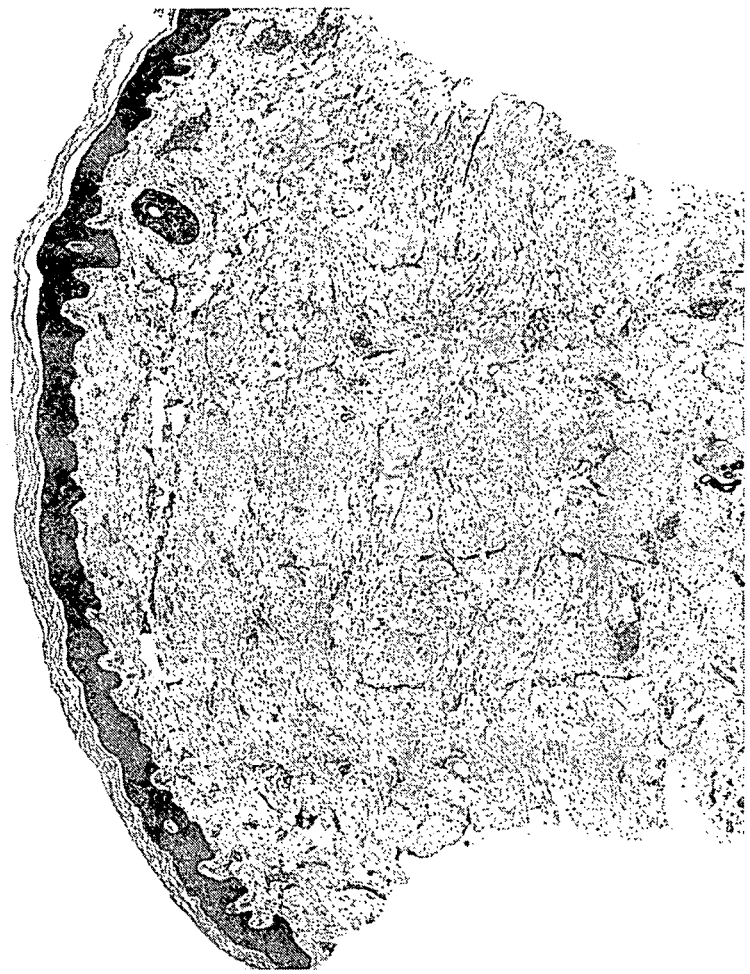
FIGURE 6: Histology samples stained with Peroxidase 120 days post-wounding for Subject 6
SUBJECT 006
TGFβ1 Stained with Peroxidase (appears as red)
Day 120 Right Full Section

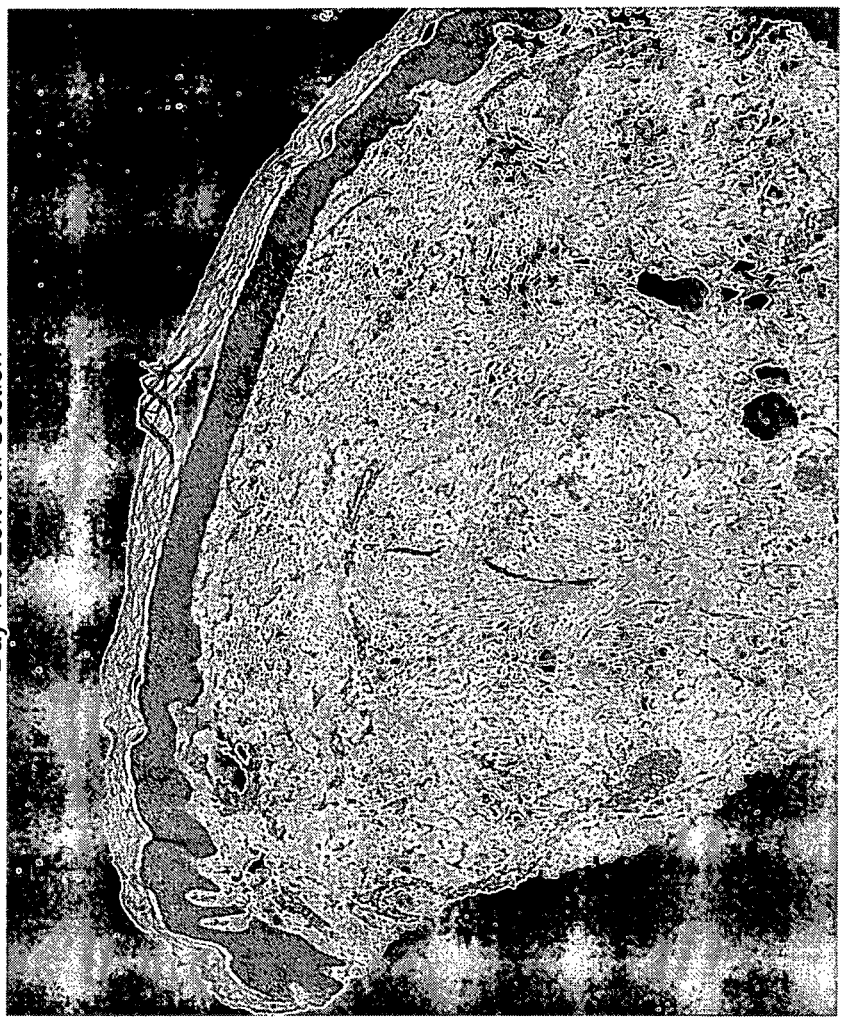
FIGURE 6 (continued): Histology samples stained with Peroxidase 120 days post-wounding for Subject 6
SUBJECT 006
TGFβ1 Stained with Peroxidase (appears as red)
Day 120 Left Full Section

PROPHYLACTIC NORMALIZATION OF CUTANEOUS WOUND REPAIR

CROSS-REFERENCE TO RELATED APPLICATIONS

The present application is a national phase entry under 35 U.S.C. § 371 of International Application No. PCT/US2015/000028 filed Feb. 18, 2015, published as WO 2015/126527 A1, which claims priority from U.S. Provisional Patent Application No. 61/941,112 filed Feb. 18, 2014, all of which are hereby incorporated herein by reference.

BACKGROUND OF THE INVENTION

Skin is the most frequently injured tissue and it is estimated that 100 million people in developed countries acquire scars each year. Injury and subsequent normal tissue repair results in a broad spectrum of scar types, ranging from fine, barely visible discolored lines to a variety of unsightly scars, including those that become stretched over time. In addition, abnormal scar formation results in pathological scars such as hypertrophic scars that are elevated but remain within the boundaries of the original lesion, and keloid scars that are elevated and spread beyond the margins of the original wound. Whether the result of normal or excessive dermal fibrosis, clinical experience shows that patients want less noticeable scars, with color and texture that closely resemble their normal skin.

Scarring is a major cause of physical and psychological morbidity. Therefore, it could be expected that patients undergoing surgical procedures are likely to be highly sensitive to scarring outcomes. Indeed, the high level of dissatisfaction with scarring outcomes among patients is reflected by the high number of patients who undergo scar revision surgery, estimated to be over 150,000 per annum in the USA. In a study published in 2009, a total of 91 percent of patients surveyed agreed that even a small improvement in scarring on a visible body site would be worthwhile. A total of 87 percent agreed that they would consider valuable any adjunct to good surgical technique to prevent or reduce scarring, with 75% of respondents agreeing that they would go to any length to minimize scarring even if the outcome resulted in small improvements in scar appearance. This data confirms that patients are highly concerned about scar appearance following surgery irrespective of age, gender, ethnic background, or geographic location.

A number of different approaches have been used in an effort to manage scarring post-surgery. These range from noninvasive techniques such as silicone gel sheeting, pressure garments, hydrating creams, and ointments to invasive techniques such as steroid injections, lasers, dermabrasion, surgery and even radiation. Unfortunately, many of these approaches are uncomfortable or burdensome for patients and many require a high level of patient compliance. Moreover, these therapies have not been proven to provide entirely satisfactory and reliable results. An increased level of understanding of the processes involved in scarring at the molecular, cellular, and tissue levels will facilitate the development of new pharmaceutical approaches to prevent or treat scarring.

Much effort has gone into identifying factors that may play a causative role in scar formation. In particular, Transforming Growth Factor beta (TGFβ) has been shown to play a role in determining the scarring outcome. TGFβ is a cytokine that has widespread effects on several aspects of growth and development, including controlling normal cellular proliferation, cellular differentiation, and other functions in many cells. The TGFβ-family of proteins includes three isoforms: TGFβ1, TGFβ2, and TGFβ3. Of these, TGFβ1 and TGFβ2 are believed to promote angiogenesis, upregulate collagen production, inhibit collagen degradation, and promote chemo-attraction of inflammatory cells; TGFβ3 is believed to be involved in cell differentiation, embryogenesis and development.

TGFβ is secreted by most cells involved in wound healing, including neutrophils, lymphocytes, macrophages, keratinocytes, dendritic cells, and fibroblasts. Research indicates that once skin is wounded, TGFβ levels rise in response to the injury and can increase the rate of healing and the breaking strength of the repaired tissue. TGFβ also enhances angiogenesis and consequent blood flow to dermal wounds, partly by stimulating the local release of other growth factors.

Some studies suggest that TGFβ1 elicits the rapid movement of neutrophils and monocytes to a wound site. In addition, in vivo animal studies suggest that exogenous TGFβ1 can increase granulation tissue, collagen formation, and wound tensile strength when applied locally or given systemically.

While increased levels of certain TGFβ isoforms are associated with normal reparative processes, increased levels of these proteins are also associated with the formation of excessive fibrous tissue, or fibrogenesis. Indeed, while TGFβ may be involved in normal wound healing and its resultant "normal" scar, hyper-expression of some TGFβ isoforms can result in overproduction of collagen fibers which in turn produces pathological scarring in the form of hypertrophic and keloid scars. Border, W. and Noble, N. (1994) New England Journal of Medicine 331: 1286-1292. For example, in rats, TGFβ1 and TGFβ2 levels are elevated in adult wounds that heal with scar formation, and this scarring can be reduced by using antibodies to inhibit TGFβ1 or TGFβ2 or by addition of TGFβ3. In addition, the addition of TGFβ1 to wounds in rat fetuses (which typically heal without a scar) can cause scar formation. Shah M et al. (1994) J Cell Sci. 107(Pt5):1137-1157.

Neurotoxin prepared from *Clostridium botulinum* bacterium, and particularly botulinum neurotoxin toxin A (BTX-A), is currently clinically used as a means of temporarily treating the underlying muscle-related factors associated with abnormal muscular spasms of the face, neck, around the eye, and for treating facial lines. BTX-A when injected into specific muscle groups around the face, causes temporary paralysis of these muscles, and thus helps decrease the spasms, as well as the appearance of the lines. In addition, recent studies have shown that deep intradermal injections of BTX-A can act on sweat glands and blood vessels.

The effects of botulinum toxin on TGFβ and wound healing have been studied. For example, studies employing a rat surgical wound model suggest that BTX-A treated wounds induce a muscular paralysis which results in a reduction in inflammation characterized by a reduction in the expression of TGFβ1 in the BTX-A treated wound. Lee, et al. Clinical and Experimental Otorhinolaryngology, Vol. 2, No. 1: 20-27, March 2009. Specifically, the authors hypothesize that the BTX-A induced muscular paralysis sub-adjacent to the wound minimizes repetitive tensile forces on the wound edges, and decreases the inflammatory and fibroblastic response, thus causing a reduction in fibrosis of the wound. The reduced expression of TGFβ1 and decreased inflammatory response at the wound site of the BTX-A group was believed due to a decrease in microtrauma resulting from the immobilization of the underlying muscle.

Additional studies teach that scar cosmesis may be achieved by immobilizing healing wounds using botulinum toxin. For example, Gassner et al. promotes the use of intramuscular injections of a chemodenervating agent such as botulinum toxin sub-adjacent to a wound to paralyze muscles capable of exerting tension on the wound during the healing process. See Gassner et al., Plast. Reconstr. Surg. 2000 May; 105(6):1948-5; U.S. Pat. No. 6,447,787.

US2006/0067950 also teaches a method of using neurotoxins for wound healing and preventing scar formation by immobilizing the area around the injured tissue by paralyzing the muscles acting on the tissue.

The possible beneficial effects of BTX-A on pre-existing, pathological hypertrophic scars has also been studied with in vitro cultures of fibroblasts isolated from hypertrophic scars. See, e.g., Xiao et al. (2009) Aesthetic Plast Surg 33:409-412; Xiao et al. (2010) Aesthetic Plast Surg 34:424-427; Xiao et al. (2011) Aesthetic Plast Surg 35:802-807. These studies report that BTX-A can inhibit the in vitro growth of fibroblasts from hypertrophic scars and reduce the expression of TGFβ1 and connective tissue growth facton expression in these cells. The authors suggest that BTX-A may have a clinical benefit in the treatment of pre-existing pathological, hypertrophic scars, however, the mechanism of action has yet to be fully appreciated.

The treatment of existing pathological keloid scars using botulinum toxin has also been postulated, but consistent results remain to be seen. U.S. Pat. No. 8,530,410 describes the administration of botulinum toxin to treat "melanin related afflictions" and "skin pigment disorders" such as keloid scars. The patent claims treating a keloid by administering botulinum toxin to the keloid using an amount less than the amount needed to paralyze a muscle. The patent also claims methods for treating a symptom associated with a keloid (i.e., pain, inflammation and vascularization) by intradermal administration of an amount of botulinum toxin less than the amount needed to paralyze a muscle. Treatment of existing dermatofibromas using intra-lesion injections and topical application of BTX-A is also disclosed in this reference. In contrast, other studies, however, teach that intralesional administration of botulinum toxin does not result in regression of keloid tissue, and does not affect the expression of extracellular matrix markers. Gauglitz et al. (2012) Skin Pharmacol Physiol 25:313-318.

Experiments in tissue repair and treatment of existing pathological scars and symptoms associated with such scarring notwithstanding, clinical success has remained elusive, and the various biological and molecular mechanisms responsible for normal tissue repair and pathological scarring have yet to be fully elucidated. Indeed, studies suggest that a potential therapeutic agent may be more or less effective depending on the type and nature of the original wound, thus a "one size fits all" clinical solution is unlikely. See, e.g., Baker et al., Dermatology Research and Practice, Vol. 2009, Article ID 625376; Gold et al. (2014) Dermatol Surg 40:817-824; Gold et al. (2014) Dermatol Surg 40:825-831. As a result, to date there is no approved pharmaceutical product in the US or the EU indicated for the reduction, improvement, or prevention of cutaneous scarring in humans. Thus, unfortunately, scar improvement and prevention of scar formation still remains an area of clearly unmet medical need.

In addition, while prophylactic measures to reduce the incidence and severity of scarring during tissue repair is desirable, there is also a need for additional clinical strategies to promote wound healing in a subject that more closely resembles normal tissue regeneration and thus facilitates the more perfect reconstruction of a wound. To date, attempts at normalization of cutaneous wound repair by promoting a regenerative healing process in injured skin (over tissue repair) include engineering the use of complex biodegradable scaffolds designed to resemble the extracellular matrix of normal skin. While such attempts have met with some success, the need for additional prophylactic methods for promoting a wound healing process in skin that involves less scarring and more tissue regeneration still exists.

SUMMARY OF THE INVENTION

Applicants have surprisingly discovered that improvement of healing outcome and a cosmetically desirable reduction in scar formation in cutaneous wounds is possible using neurotoxin without requiring the paralysis of the musculature adjacent and/or sub-adjacent to the wound. Specifically, prior to the studies disclosed herein, the inventors were unaware of any studies demonstrating the inhibition of scar formation in vivo by superficial intradermal injection of neurotoxin and without paralysis of the surrounding musculature.

Accordingly, in one aspect, the invention is directed to a method of decreasing scar formation in a skin wound in a subject in need thereof comprising administering to said subject in or near said wound an effective amount of one or more neurotoxins, wherein said amount is sufficient to decrease formation of scar tissue and insufficient to produce muscular paralysis in said wound.

Applicants have also discovered that the administration of neurotoxin as provided herein can produce healing which more closely resembles tissue regeneration, and thus can be used to create skin morphology at the wound site that more closely resembles uninjured tissue. Thus, in another aspect, the invention is directed to a method of promoting tissue regeneration in a skin wound in a subject in need thereof comprising administering to said subject in or near said wound an effective amount of one or more neurotoxins, wherein said amount is sufficient to promote regeneration of skin morphology in said wound characteristic of dermis in uninjured skin. In a particular embodiment, said skin morphology is characterized by the formation of rete-ridges and/or collagen deposition in the wound that more closely resembles that seen in uninjured tissue.

In a particular embodiment, the neurotoxin is botulinum neurotoxin or a derivative thereof. In particular embodiments the botulinum neurotoxin is selected from the group consisting of botulinum neurotoxin A, B, C, D, E, F, and G. In a particular embodiment the botulinum neurotoxin is botulinum neurotoxin A or a derivative thereof. In additional embodiments, the botulinum neurotoxin type A is incobotulinumtoxinA. In another embodiment, the botulinum neurotoxin type A is onabotulinumtoxinA. In another embodiment, the botulinum neurotoxin type A is abobotulinumtoxinA. In another embodiment, the botulinum toxin is botulinum neurotoxin B or a derivative thereof. In a particular embodiment, the botulinum neurotoxin B is rimabotulinumtoxinB.

In another aspect, the methods of the invention further comprise administering one or more additional agents in addition to the neurotoxin, in or near said wound. In particular embodiments the additional agent is administered prior to administration of said neurotoxin, after administration of said neurotoxin, and/or concurrently with the administration of said neurotoxin.

In particular embodiments, the neurotoxin and/or the additional agent is administered in or near the wound in a manner selected from the group consisting of intradermal injection, superficial intradermal injection, jet nebulizer injection, topical application, or a combination thereof. In particular embodiments, the neurotoxin and/or the additional agent may be topically applied in the form of a cream, ointment, a transdermal patch or a transdermal disc.

In a particular embodiment, the neurotoxin and/or the additional agent is administered by superficial intradermal injection in or near the wound site to form a bleb of neurotoxin and/or agent superficially intradermally in or near the site of the wound.

In particular embodiments, the neurotoxin is diluted prior to injection. In a further embodiment, aliquots of diluted neurotoxin are injected into the superficial dermal or epidermal/dermal junction creating one or more bleb reservoirs of neurotoxin.

In a particular embodiment, said aliquots are from about 0.02 ml per cm$^2$ to about 0.2 ml per cm$^2$ per injection.

In particular embodiments, the neurotoxin is incobotulinumtoxinA and said incobotulinumtoxinA is superficially injected in an amount from about 2.5 units/cm$^2$ to about 7.5 units/cm$^2$ per injection. In a particular embodiment, the incobotulinumtoxinA is administered at a dose of about 7.5 units/cm$^2$ per injection. In another particular embodiment, the incobotulinumtoxinA is administered at a dose of about 5.0 units/cm$^2$ per injection. In another particular embodiment, the incobotulinumtoxinA is administered at a dose of about 2.5 units/cm$^2$ per injection.

In a particular embodiment, one or more superficial intradermal injections are performed in the wound itself and/or in or near the wound. In a particular embodiment, the injections are made in the wound margin from about 0 cm to about 5 cm from the wound. In a particular embodiment, the injections are made in the wound margin within about 3 cm from the wound. In another embodiment the injections are made around the entire wound site, or in one or more subsections thereof.

In one embodiment, the additional agent is selected from the group consisting of anesthetics, antimicrobials, and vasoconstrictive agents.

In one embodiment, the additional agent is an anesthetic. In particular embodiments, the anesthetic is selected from the group consisting of lidocaine, bupivacaine, and mepivacaine.

In one embodiment, the additional agent is a vasoconstrictive agent. In a particular embodiment the vasoconstrictive agent is selected from the group consisting of amphetamines, antihistamines, decongestants, and other agents capable of enhancing norepinephrine, epinephrine, or adrenergic activity by stimulating α-adrenergic receptors.

In another embodiment, the additional agent is an agent capable of enhancing skin repair, skin regeneration and/or wound healing. For example, in a particular embodiment the agent may be a growth factor, a cytokine, a protein such as integrins, canonical Wnt proteins, and connexin 43; an inhibitor or activator of a growth factor or a cytokine or a protein such as integrins, canonical Wnt proteins, and connexin 43, an antagonist or agonist of a growth factor receptor or cytokine receptor, or protein such as integrins, canonical Wnt proteins, and connexin 43; or a combination thereof. In a particular embodiment, the additional agent can inhibit expression and/or activity of a growth factor or a cytokine.

In a particular embodiment said agent can inhibit the expression and/or activity of one or more proteins selected from the group consisting of homeobox proteins, early growth protein 1, vascular endothelial growth factor, insulin-like growth factor, integrins, canonical Wnt proteins, connexin 43, and TGFβ.

In another embodiment, the agent is one or more autologous blood products. In another embodiment, the agent is one or more minimally altered autologous blood products. In various embodiments, such minimally altered autologous blood products are selected from the group consisting of interleukins, platelet derived growth factors, and connective tissue growth factor. In another embodiment, the autologous blood product is platelet-rich plasma.

In another embodiment the neurotoxin and/or the additional agent are modified, formulated, and/or administered to optimize the activity of the toxin and/or the additional agent in the superficial layers of the skin in or near the site of the wound, including at the wound margins.

In a particular embodiment, the neurotoxin and/or the additional agent are modified, formulated and/or administered in a manner designed to minimize diffusion and/or dispersion of the neurotoxin or additional agent away from the site of administration.

As contemplated herein, additional aspects of the present invention include use of one or more neurotoxins for the preparation of a medicament for inhibiting scar formation in a skin wound, and use of one or more neurotoxins for promoting tissue regeneration in a skin wound. As contemplated herein, the neurotoxins may be used alone, or in conjunction with one or more additional agents.

BRIEF DESCRIPTION OF THE DRAWINGS

FIG. 1: Photographs of wound sites at 120 days post-wounding for Subject 3.

FIG. 2: Left (BTX-A) distal 3-dimensional image 120 days post-wounding for Subject 3.

FIG. 3: Right (Placebo) distal 3-dimensional image 120 days post-wounding for Subject 3.

FIG. 4: Histology samples stained with peroxidase 120 days post-wounding for Subject 3. The darker the color of the stain (red stain in original photo), the greater the expression of TGFβ1.

FIG. 5: Photographs of wound sites at 120 days post-wounding for Subject 6.

FIG. 6: Histology samples stained with peroxidase 120 days post-wounding for Subject 6. As depicted in the figures, the darker the color of the stain (red stain in original photo), the greater the expression of TGFβ1.

DETAILED DESCRIPTION

While the specification concludes with the claims particularly pointing and distinctly claiming the invention, it is believed that the present invention will be better understood from the following description.

Any percentages and ratios used herein are by weight of the total composition unless otherwise indicated herein. All measurements made are at 25° C. and normal pressure unless otherwise designated. All temperatures are in Degrees Celsius unless specified otherwise. The present invention can "comprise" (open ended) or "consist essentially of" the components of the present invention as well as other ingredients or elements described herein. As used herein, "comprising" means the elements recited, or their equivalent in structure or function, plus any other element or elements which are not recited. The terms "having" and "including" are also to be construed as open ended unless the context suggests otherwise.

All ranges recited herein include the endpoints, including those that recite a range "between" two values. Terms such as "about," "generally," "substantially," and the like are to be construed as modifying a term or value such that it is not an absolute, but does not read on the prior art. Such terms will be defined by the circumstances and the terms that they modify as those terms are understood by those of skill in the art. This includes, at very least, the degree of expected experimental error, technique error and instrument error for a given technique used to measure a value.

Unless otherwise indicated, as used herein, "a" and "an" include the plural, such that, e.g., "a neurotoxin" can mean at least one neurotoxin, as well as a plurality of neurotoxins, i.e., more than one neurotoxin, including but not limited to, neurotoxins of different types.

Where used herein, the term "and/or" when used in a list of two or more items means that any one of the listed characteristics can be present, or any combination of two or more of the listed characteristics can be present. For example, if a composition is described as comprising agents A, B, and/or C, the composition can comprise A feature alone; B alone; C alone; A and B in combination; A and C in combination; B and C in combination; or A, B, and C in combination.

All references cited herein are hereby incorporated by reference in the entirety.

As disclosed herein, it has been surprisingly discovered that the superficial intradermal injection of a neurotoxin in or around a skin wound, and particularly in the margins of a skin wound, can contribute to a reduction in scar formation associated with the healing of the wound. As understood by one of skill in the art and as used herein, a "superficial" intradermal injection refers to an injection in which a substance is placed in the upper dermis and/or near the epidermal/dermal junction. For example, in one possible method, a superficial injection may be performed by introducing the needle into the skin at an angle from about 10 degrees to less than 90 degrees in a manner such that needle placement through the skin facilitates the placement of the toxin in the uppermost superficial layer of dermis. Superficial intradermal injections differ from intradermal injections in which a needle is inserted deeper into the skin and perpendicular to the skin, and which cannot be used to produce a bleb of injected substance as contemplated herein.

The present invention relates to a method to achieve normalization of tissue repair in a prophylactic sense, i.e., by preventing or inhibiting de novo scar formation in a skin wound during the healing process.

Notably, the observed inhibition in scar formation reported herein occurs without requiring the concomitant muscular paralysis in the tissue adjacent and/or sub-adjacent to the wound which has previously been deemed critical in the process of botulinum toxin-induced scar cosmesis. Thus, one objective of this disclosure is to describe a method of treating a patient with a wound on the skin in order to prevent or minimize the formation of scar tissue during the process of tissue repair without also inducing muscular paralysis in the subject.

Specifically, in one aspect, the invention is directed to a method of inhibiting scar formation in a skin wound in a subject in need thereof comprising administering to said subject in or near said wound an effective amount of one or more neurotoxins, wherein said amount is sufficient to inhibit formation of scar tissue and insufficient to produce muscular paralysis in said wound.

It is particularly contemplated herein that the cosmetic outcome of scar formation of a cutaneous wound in a patient can be improved using a superficial intradermal injection of botulinum toxin type A (BTX-A) into the margins of a cutaneous wound, e.g., at the time of surgery or other clinical treatment of the wound.

In addition, it has been surprisingly discovered that superficial intradermal injections of toxin as disclosed herein promotes the formation of more morphologically normal rete-ridges, i.e., rather than the formation of a flattened epidermal/dermal junction typically seen in hypertrophic or keloid scars. In addition, superficial intradermal injections of toxin such as described herein can promote collagen distribution similar to that seen in uninjured tissue, i.e., the orientation of collagen fibers during the healing process are more naturally ordered, e.g., oriented in the plane of the wound, rather than in a random fashion. Without intending to be bound by any particular theory, it is hypothesized that by altering cytokine expression in the treated wound, the methods of the present invention facilitate the process by which the body can heal itself by tissue regeneration, rather than by tissue repair which is associated with scar formation.

Accordingly, the results provided herein indicate that administration of neurotoxin as contemplated herein can stimulate wound healing that can produce a more normal skin morphology such as produced during tissue regeneration in uninjured skin. Thus, in another aspect, the invention relates to a method of promoting tissue regeneration in a skin wound in a subject in need thereof comprising administering to said subject in or near said wound an effective amount of one or more neurotoxins, wherein said amount is sufficient to promote regeneration of skin morphology in said wound characteristic of dermis in uninjured skin. In a particular embodiment, said skin morphology is characterized by the formation of rete-ridges and/or collagen deposition that are more typical of uninjured tissue.

As used herein, "wound" refers to skin (cutaneous) wounds, and includes any and all types of wounds (including burns) to which administration of neurotoxin as disclosed herein can provide a therapeutic (e.g., cosmetic) effect. Such wounds include but are not limited to skin wounds that are the result of accidents or are the result of surgical procedures. In particular, surgically introduced incisions include scar revision excision surgery. As such, a skin wound includes elective incisions and non-elective incisions, abrasions and thermal injuries.

Accordingly, "a subject in need thereof" refers to any living organism suffering from a wound (accidental or surgical) in which inhibition of scar formation, and promotion of mound healing characteristic of skin regeneration is desirable. Human patients, as well as animals may be treated according to the methods of the present invention.

The term "scar" or "scar tissue" as used herein is understood by one of skill in the art and includes both normal scars formed during tissue repair as well as pathological scars, e.g., scars formed by excessive fibrosis, e.g., hypertrophic scars or keloid scars.

As used herein, the terms, "decreasing scar formation", "decreasing formation of scar tissue", "inhibiting scar formation", "inhibition of formation of scar tissue", "inhibition of scar formation" and like terms are used interchangeably herein and refer to a prophylactic effect on scar formation such that the tendency of the wound to form a scar is decreased or otherwise reduced compared to an untreated wound. As understood herein, the terms encompass prophylactic effects on the formation of excessive fibrotic scar tissue characteristic of pathological scars. As contemplated herein, the terms encompass any amount of prevention, reduction or amelioration in the incidence, degree, or severity of scar formation which produces a cosmetically more desirable scar, e.g., a scar which is less noticeable in the skin. In this regard, techniques for assessing and grading the severity of scar formation, and patient satisfaction regarding same, are familiar to one of skill in the art, and include various objective methodologies including, e.g., visual assessment and physical palpation of the scar tissue.

Thus, as used herein, an "effective amount" of neurotoxin or other agent for use in the methods of the present invention is that amount necessary to achieve the desired prophylactic effect on the inhibition of scar formation and/or produce skin morphology more like uninjured tissue, e.g., to produce a normalization of cutaneous wound repair in a subject in need thereof. Specifically, the term includes that amount of a compound effective to prevent, alleviate or ameliorate the formation of a scar in a cutaneous wound.

Determination of an "effective amount" of a neurotoxin, or other agent to be used in combination with a neurotoxin according to the disclosed methods, is well within the capability of those skilled in the art, especially in light of the detailed disclosure provided herein. For example, in cases of local administration of a drug, one of skill in the art appreciates that the effective local concentration of the drug may not be related to plasma concentration, and other procedures known in the art may be employed to determine the correct dosage amount and interval. The amount of a composition administered will, of course, be dependent on factors including, e.g., the subject being treated, the severity and nature of the wound, the manner of administration, and the judgment of the prescribing physician.

An "effective amount" can be determined by one of skill in the art according to conventional methods. It should be noted that while amounts of neurotoxin sufficient to paralyze a muscle could be used, muscular paralysis is not achieved because the injections are limited to intradermal injections or topical application as disclosed herein.

Indeed, while amounts of neurotoxin sufficient to produce muscular paralysis (if injected intramuscularly) can be used, notably, the methods of the present invention do not require neurotoxin-induced temporary muscular paralysis such as that typically achieved during FDA-approved cosmetic use of botulinum toxin. Thus, the amount of toxin used according to the present invention can be less than this amount. In this regard, when partial or total muscular paralysis is desired, rather than a strict standard, one of skill in the art appreciates that doses in total units per treatment area can vary depending on several factors, e.g., the concentration of the neurotoxin, the method of intramuscular injection, as well as the unique characteristics of the patient (e.g., body size and gender) and the muscle being treated, including subjective observations of muscle mass, strength, size and location.

With an understanding of such factors, including but not limited to the variability in activity of commercial formulations of neurotoxin, one of skill in the art appreciates that the actual dosage amount for use in the methods of the instant invention (e.g., total Units administered) can vary, and may be determined by the skilled practitioner.

Indeed, the amount of neurotoxin may vary depending on the activity of a particular formulation of toxin and/or the commercial source. For example, as evidenced in the data in the below examples, dosage amounts of incobotulinumtoxinA obtained from Merz Pharmaceuticals for use in the instant invention may range from about 2.5 units/cm$^2$ to about 7.5 units/cm$^2$. In a particular embodiment, the neurotoxin may be administered at a dose of about 7.5 units/cm$^2$. In another embodiment, the neurotoxin may be administered at a dose of about 5.0 units/cm$^2$. In another embodiment, the neurotoxin may be administered at a dose of about 2.5 units/cm$^2$.

Moreover, commercial formulations of "BOTOX" (Allergan, Irvine, Calif.) may be used for cosmetic purposes at less than 2.5 units/cm$^2$, less than 5.0 units/cm$^2$, or less than 7.5 units/cm$^2$. In contrast, commercial formulations of DYSPORT (Galderma Laboratories, Ft. Worth, Tex.) may be used at less than 7.5 units/cm$^2$; less than 15 units/cm$^2$; and less than 22.5 units/cm$^2$. In one possible embodiment, these treatments could be administered, e.g., by superficial intradermal injections within 0 cm to 5 cm from the wound (i.e., in the wound margins), one injection per cm2 tissue, forming a bleb intradermally, for over approximately a 6 month period of time, or less, beginning any time ranging from immediately post injury up to approximately 6 months thereafter, contemplating an initial treatment followed by approximately 2 to 6 repeat treatments during that period of time.

Because the activity of commercial batches of neurotoxin can vary, commercial formulations of neurotoxins are often diluted before administered to decrease wrinkles and fine lines. Similarly, as understood herein, one of skill in the art can determine the appropriate dilution and resulting concentration of neurotoxin for use in the instant invention without undue experimentation. Specifically, as contemplated herein, commercial formulations of neurotoxins may be diluted prior to administration according to the methods of the instant invention using conventional methods and a variety of suitable pharmaceutically acceptable agents. These reagents include, e.g., commercial available saline solutions, e.g., 0.9% sodium chloride preservative free, or bacteriostatic water.

As used herein, the "margins" of a wound refer to the peripheral tissue immediately surrounding the wound, e.g., within from about 0 cm to about 5 cm from the site of the wound, but not including the wound proper.

In addition, as used herein, "at, in, or near said wound", "in or near said wound", or "in or near the site of the wound" and like terms refer to administration of a neurotoxin and/or other additional agent at the wound site, including in the margins or the wound and surrounding tissue, and/or in the wound (injured tissue) itself. For example, as contemplated herein, one or more neurotoxins, alone or in combination with one or more other agents, may be administered by one or more (e.g. repeated) intradermal injections distributed in the wound, and/or anywhere in the tissue surrounding the wound. Topical administration of one or more active compounds in the same manner at the wound site is also contemplated herein.

As contemplated herein, in one embodiment, injections and/or topical administration of one or more active compounds may be administered repeatedly according to the methods of the instant invention as early as immediately post injury and up to approximately 6 months post injury. Final scar formation is believed to occur approximately 6 months post injury, thus treatment any time prior to final scar formation may provide a prophylactic benefit on scar formation and/or tissue regeneration.

As understood herein, while the methods of the present invention may be used for treating existing scars, the methods of the instant invention are primarily intended as a method for normalizing tissue repair and ideally promoting tissue regeneration early in the wound healing process.

Notably, the beneficial effects achieved according to the methods of the instant invention may be obtained without the concomitant muscular paralysis associated with other methods. Without intending to be bound to any particular mechanism of action, it is contemplated herein that intradermal administration of a neurotoxin at a wound site in a subject, and particularly superficial intradermal injections which produce bleb reservoirs of neurotoxins and other healing agents in concentrated effective amounts close to the wound site, may have cosmetic and/or therapeutic usefulness by providing these products to the dermis and epidermis where the signaling for fibrosis actually occurs.

Indeed, by providing effective concentrations of neurotoxin and other active agents at the level of the dermis, where the biological signaling mechanisms involved in tissue repair, fibrosis, and tissue regeneration occur, the methods of the instant invention are very different from prior art techniques which employ intramuscular injections to induce muscular paralysis. As one of skill in the art would appreciate, intramuscular injections to produce paralyzing effects on the underlying musculature and thus reduce wound tension would be unlikely to affect biological processes which occur at the level of the dermis, including the wound healing cascade and/or tissue regeneration.

Accordingly, without intending to be bound to any particular theory of operation, it is contemplated herein that prophylactic benefits on scar formation and/or on tissue regeneration may be achieved according to the methods of the instant invention by modulating one or more cytokines or other growth factors at the level of the dermis. This includes, e.g., decreasing the expression and/or activity of one or more TGFβ isoforms responsible for scar formation in vivo, and/or by increasing the expression and/or activity of one or more TGFβ isoforms that inhibit scar formation in vivo. Specifically, as demonstrated in the below examples, it is believed that one possible mechanism involves the suppression of TGFβ1 and TGFβ2 expression by botulinum toxin type A in the dermal tissue surrounding a wound, and this suppression can inhibit and/or otherwise minimize or eliminate the formation of scar tissue in the wound site as the wound heals.

The postulated role of TGFβ isoforms is likely only part of a cascade of events leading to scar formation. Thus, in addition to the potential effects on TGFβ isoforms, it is contemplated herein that the administration of neurotoxin as disclosed herein promotes the beneficial activity of other cytokines or growth factors and/or may promote a reduction in levels of unfavorable cytokines or growth factors at the level of the dermis which not only can minimize the formation of fibrotic tissue during tissue repair, but also supports conditions in vivo necessary to promote the process of tissue regeneration.

As used herein, "normalization of cutaneous wound repair" refers to promoting tissue healing that produces skin morphology which more closely resembles uninjured tissue, and is less likely to form a cosmetically undesirable scar at the wound site. Indeed, as understood by one of skill in the art, tissue "repair" is distinct from tissue "regeneration"; the former results in healed skin that can show visible evidence of scarring as well as less evident disruptions in the normal morphology of the skin. In contrast, tissue regeneration occurs without disruption to normal skin morphology and function and resembles the regenerative process that normally occurs in uninjured skin. Thus, ideally, the methods of the present invention not only contemplate the use of neurotoxin in a method of inhibiting scar tissue during wound repair, but also in a method which can promote tissue regeneration at the site of a skin wound.

In addition, while the present invention is useful to achieve a visible effect on resultant wound healing by inhibiting scar formation and promoting a normal, i.e., uninjured, skin morphology, effects achieved as a result of superficial intradermal injection of toxin on the dermal level can also produce a beneficial effect on the ultimate strength of the healed wound. Such difference in healing produces an actual physical difference in the site of the wound which is evident to one of skill in the art upon palpation; e.g., the skin is less indurated, softer, and less elevated in comparison to scar tissue. Such improvement in wound strength and physical attributes are very desirable to patients.

As contemplated herein, neurotoxins for use according to the methods of the present invention include one or more Clostridial neurotoxins. These include botulinum toxins. As used herein, "botulinum toxins" include the biological neurotoxins botulinum neurotoxin type A and botulinum neurotoxin type B produced by the bacterium *Clostridium botulinum* which are capable of, and used by clinicians for, blocking neuromuscular transmissions.

Clostridial toxins for use in the disclosed methods include, e.g., onabotulinumtoxinA, abobotulinumtoxinA, incobotulinumtoxinA, and rimabotulinumtoxinB. Various formulations suitable for use in humans are commercially available and are familiar to one of skill in the art, including, e.g., "NeuroBloc®" (preparation of rimabotulinumtoxinB Europe/US WorldMeds, Louisville, Ky.); "Botox®" (preparation of onabotulinumtoxinA; Allergan, Inc. Irvine, Calif.); "Dysport®" (preparation of abobotulinumtoxinA, Galderma Laboratories, Ft. Worth, Tex.); and "Xeomin®" (preparation of incobotulinumtoxinA; Merz Pharmaceuticals GmbH, Frankfurt, Germany.)

As contemplated herein, the methods of the present invention comprise administration of one or more neurotoxins in any manner of administration suitable for delivering the compound to the wound site in order to achieve the objectives of the methods of the present invention. Thus, the term "administering" as used herein includes any clinically acceptable means of delivering a neurotoxin, or any other agent, for the cosmetic and/or therapeutic uses disclosed herein. Suitable conventional pharmaceutical materials and methods for such administration are familiar to one of skill in the art.

Notably, as discussed above, it is contemplated herein that the use of one or more neurotoxins may prove useful in accordance with the methods of the present invention when administered in a manner which does not require intramuscular injection. Thus, in particular embodiments, it is contemplated herein that topical application, as well as superficial intradermal injection of a neurotoxin may be used in accordance with the disclosed methods.

Moreover, as contemplated herein, the methods of the present invention are performed, and beneficial effects are obtained, using an amount of neurotoxin which is less than what is typically administered to achieve temporary muscle paralysis in conventional cosmetic procedures. Thus, as discussed above, an "effective amount" of a neurotoxin encompasses an amount sufficient to achieve the intended purpose, i.e., prophylactically inhibiting scar formation and promoting a normal, i.e., uninjured, skin morphology. This amount is less than what is typically required to produce muscular paralysis in the underlying musculature, i.e., insufficient to reduce tension within muscles in and near the site of a wound. Such amount may be determined by one of skill in the art as discussed above. For example, treatment for muscle spasticity with botulinum toxin typically requires 5 units per kilogram to 25 units per kilogram of body weight of onabotulinumtoxinA; typically, a dose for a young adult would be 250 units to 1250 units. See, e.g., Placzek R et al. (2010) Toxins 2; 2258-2271. The use of modified forms and/or derivatives of neurotoxins (e.g., which do not produce muscular paralysis) are contemplated herein. Such forms may be produced by one of skill in the art according to conventional methods.

As discussed above, one or more neurotoxins may be used alone, or in combination with another neurotoxin according to the methods of the present invention. They may be administered alone, sequentially, and/or in any combination.

It is further contemplated herein that one or more neurotoxins might have a beneficial, prophylactic effect on cutaneous wound repair and/or tissue regeneration in combination with another agent. Thus, it is contemplated herein that one or more neurotoxins may be used in the disclosed methods in combination with a variety of additional cosmetic or pharmaceutically acceptable agents as discussed in detail below.

Such neurotoxins and additional agents may be administered to a subject according to a variety of pharmaceutically and clinically acceptable strategies. These include, e.g., preparation and administration of a formulation comprising one or more neurotoxins alone, or in combination with one or more additional therapeutic agents. Alternatively, one or more neurotoxins may be co-administered with one or more other therapeutic agents by separate injections or other means of administration. In addition, one or more additional therapeutic agents can be administered separately prior to injection of the neurotoxin or after the injection of the neurotoxin.

The preparation of formulations and dosage forms of neurotoxins and other agents for use in the methods of the present invention (alone or in combination) are familiar to one of skill in the art and can be achieved using conventional methods. Techniques for formulation and administration of drugs may be found in "Remington's Pharmacological Sciences," Mack Publishing Co., Easton, Pa., latest edition.

As contemplated herein, the neurotoxins and other agents may be administered at a wound site according to the methods of the present invention by any clinically acceptable method which can achieve the desired results. In a particular embodiment, the neurotoxin and/or additional agent may be administered topically. Various means for the topical administration of agents are familiar to one of skill in the art and include, for example, topical pharmaceutical compositions such as dispersions, suspensions, solutions, emulsions, patches, discs, gels, powders, ointments, creams, pastes, plasters, lotions, sprays, foams, aerosols (propellant based or non-propellant based) and the like.

Other means for topical delivery of neurotoxins and/or other active agents suitable for use in the methods of the present invention include pharmaceutically acceptable drug delivery devices such as transdermal delivery systems. Such delivery systems include, e.g., adhesive patches or discs containing one or more drugs suitable for transdermal drug delivery. Such pharmaceutically acceptable drug delivery devices and the use thereof are familiar to one of skill in the art. For transdermal administration, penetrants appropriate to the barrier to be permeated may be used in the formulation. Such penetrants are generally known in the art. Also, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes.

As discussed herein, the neurotoxins and agents may also be delivered by one or more intradermal injections, including one or more superficial intradermal injections, in or near the site of the wound to be treated. As understood by one of skill in the art and as discussed hereinabove, a "superficial" intradermal injection refers to an injection in which a substance is placed in the upper dermis. It is contemplated herein that the neurotoxin (or other agent) may be superficially intradermally injected as a bleb. The bleb of toxin can act as a reservoir or depot of toxin in the dermis (evidenced by visible skin blanching).

While not typically used to administer neurotoxins, superficial intradermal injections are familiar to one of skill in the art. Such technique is commonly used, e.g., in the administration of the Mantoux tuberculin skin test and in LAVIV (azficel-T) autologous cell therapy. As contemplated herein, in one possible method, a superficial injection may be performed by introducing the needle into the skin at, in or near the wound site at an angle from about 10 degrees to less than 90 degrees in a manner such that needle placement through the skin facilitates the placement of the toxin in the uppermost superficial layer of dermis.

As understood by the skilled practitioner, superficial intradermal injections differ from intradermal injections in which a needle is inserted deeper into the skin and perpendicular to the skin, and which typically are not used to produce a bleb of injected substance.

As contemplated herein, intradermal and superficial intradermal injections may be performed in accordance with the methods of the instant invention using conventional materials available from a variety of commercial vendors, e.g., using sterile, small gauge size needles such as 27 G through 32 G.

It is further contemplated herein that neurotoxins and other agents disclosed herein may be administered according to the methods of the instant invention using a jet nebulizer. Techniques for administration of such injections are familiar to one of skill in the art, and devices for such use are commercially available.

For injection, neurotoxins and/or other agents for use in the disclosed methods of the invention may be formulated in aqueous solutions, preferably in physiologically compatible buffers, buffers with or without a low concentration of surfactant or cosolvent, or physiological saline buffer. Formulations for injection may be presented in unit dosage form, e.g., in aliquots or ampoules or in multi-dose containers, with an added preservative. The compositions may take such forms as suspensions, solutions, or emulsions in oily or aqueous vehicles, and may contain formulating materials such as suspending, stabilizing and/or dispersing agents.

The active ingredient may be in powder form for constitution with a suitable vehicle, e.g., sterile, pyrogen-free water, before use.

Pharmaceutically acceptable carriers familiar to one of skill in the art may be used in formulating compositions of neurotoxins and/or other agents and include, e.g., various commercially available physiologically acceptable vehicles, adjuvants, excipients, and diluents. In a particular embodiment, diluents for use with the neurotoxins of the present invention include, but are not limited to, pharmaceutically acceptable formulations of 0.9% sodium chloride. The pharmaceutical compositions herein also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

As understood by one of skill in the art, dosage amounts of one or more neurotoxins and/or additional agents suitable for use with the claimed methods may vary and may be determined by one of skill in the art without undue experimentation. As discussed infra, dosage amounts may vary depending on concentration strength and activity of the active substances to be administered, and can be determined by one of skill in the art. As discussed above, different forms of botulinum toxin (even in the same class) may be used in various doses based on their individual properties.

As contemplated herein, other agents for use in combination with one or more neurotoxins in the methods of the instant invention include anesthetics, particularly local anesthetics. In some embodiments, the neurotoxin may be co-administered with an anesthetic, or administered separately. In some embodiments, the anesthetic is injected. In other embodiments, the local anesthetic is applied topically to the skin. In further embodiments the local anesthetic is selected from the group consisting of lidocaine, bupivacaine, or mepivacaine.

In addition, it is further contemplated herein that the neurotoxin formulations for use according to the methods of the present invention may be used in combination, and/or formulated to contain other active agents, e.g., agents that can provide an antimicrobial effect. For example, pharmaceutical formulations comprising one or more botulinum toxins and one or more active antimicrobial agents are contemplated herein. Such antimicrobial are familiar to one of skill in the art and are commercially available and include, e.g., bacteriostatic water, which is sterile non-pyrogenic water that contains 0.9% benzyl alcohol (9 mg/mL), added as a bacteriostatic preservative.

As discussed above, without being bound by a particular mechanism of action, it is believed that rather than reducing tension within muscles in or near the site of a wound, the demonstrated beneficial effects of superficial intradermal administration of neurotoxin may be due to stimulatory and/or inhibitory effects of the neurotoxin on one or more biological molecules involved in the healing cascade, e.g., on the production and/or activity of certain growth factors or cytokines in the area of the wound. Moreover, it is postulated herein that administration of neurotoxin as disclosed herein may alter growth factor or cytokine expression in the area of a wound so that it more closely resembles growth factor or cytokine expression characteristic of normal tissue regeneration. Thus, additional agents contemplated for use in combination with neurotoxins in the methods of the instant invention include one or more additional cytokines or growth factors, inhibitors and/or activators of various cytokines and growth factors, and/or agonists and antagonists of growth factor or cytokine receptors. One of skill in the art having an understanding of the biological processes associated with tissue repair and regeneration will appreciate the particular compounds best suited for such use, and can thus arrive at particular combinations for use in the methods of the instant invention without undue experimentation. Growth factors and cytokines that may play a role in the processes of tissue repair and/or tissue regeneration are disclosed in the literature, including, e.g., in Namazi et al., (2011) International Journal of Dermatology 50: 85-93.

For example, as contemplated herein, such combinations may include compounds which can be used to inhibit one or more biological molecules associated with biological pathways which can produce excessive collagen formation or tissue fibrosis. Thus, it is contemplated that the activity and/or synthesis of certain isoforms of TGFβ may be affected by neurotoxin. Among the possible mechanisms of action, the reduction in TGFβ subtypes TGF-β1 and/or TGF-β2 by superficial intradermal application of toxin may reduce the tendency of the skin to form a scar by decreasing TGF-β induced collagen formation. Thus, in a particular embodiment, the method includes administration of an additional agent which can also inhibit the synthesis and/or activity of TGFβ1 and/or TGFβ2, and/or potentiate the inhibitory effects of neurotoxin in this regard. Such compounds or agents may also include, e.g., TGFβ1 or TGFβ2 receptor antagonists and may be administered alone or together, and optionally, may be administered in combination with a compound or other agent which can stimulate the synthesis and/or activity of TGFβ3, e.g., a receptor agonist. Inhibitors and activators (antagonists and agonists) of TGFβ isoforms suitable for pharmaceutical use are familiar to one of skill in the art and are commercially available, e.g., from Selleck Chemicals (Boston, Mass.).

In addition to the foregoing, it is further contemplated herein that neurotoxins may be administered as disclosed herein in combination with one or more additional cytokines or growth factors, inhibitors and/or activators of various cytokines and growth factors, and/or agonists and antagonists of growth factor or cytokine receptors; and/or other proteins such as integrins, canonical Wnt proteins, and connexin 43 and/or inhibitors and/or activators thereof; which can produce beneficial effects on skin repair and/or skin regeneration. Without being bound to any particular mechanism of action, it is contemplated herein that such growth factors, cytokines, and inhibitors and/or activators thereof may facilitate desirable tissue repair and/or tissue regeneration when used in combination with one or more neurotoxins, e.g., by stimulating normal collagen production; reducing inflammation; altering angiogenesis; promoting cell growth and multiplication; regulating cell growth and division; increasing number of white blood cells and/or stimulating epithelial cell growth.

Thus, it is contemplated herein that additional compounds suitable for use in the methods of the instant invention as agents for use in combination with neurotoxins include, for example, vascular endothelial growth factor (VEGF); hepatocyte growth factor (HGF); keratinocyte growth factor (KGF); interleukins (IL-6, IL-7, IL-8); basic fibroblast growth factor (bFGF); insulin-like growth factor 1 (IGF1); platelet-derived growth factor AA (PDGF-AA); and granulocyte monocyte colony stimulating factor (GMCSF). Inhibitors or other modulators of activity of such compounds and other growth factors are also contemplated herein, including agents that can inhibit the expression and/or activity of homeobox proteins, early growth protein 1, vascular endothelial growth factor, insulin-like growth factor, integrins, canonical Wnt proteins, connexin 43, or TGFβ. One of skill in the art appreciates that the action of such growth factors and cytokines, receptor agonists and antagonists thereof, and growth factor and cytokine inhibitors and activators can vary depending on the activity of other such factors used in combination. Suitable combinations may be formulated accordingly by a skilled practitioner. Growth factors and cytokines, receptor agonists and antagonists thereof, and growth factor and cytokine inhibitors and activators suitable for pharmaceutical use in the methods of the instant invention are available from a variety of commercial vendors, e.g., from GenScript USA Inc., (Piscataway, N.J., and Selleck Chemicals (Boston, Mass.).

In addition to the foregoing, it is contemplated herein that neurotoxins may be administered according to the methods of the present invention in combination with one or more autologous blood products, including minimally altered autologous blood products. Such products are familiar to one of skill in the art and include, e.g., minimally altered autologous blood products such as interleukins, platelet derived growth factors, or connective tissue growth factor.

In addition, the use of platelet-rich-plasma (PRP) is contemplated herein. Platelet-rich plasma has been used in various clinical applications; its healing effects are believed caused by growth factors released from the platelets which may induce a healing response. Such blood products may be produced and/or obtained according to conventional methods familiar to one of skill in the art including, e.g., centrifugation of a small sample of whole blood collected from the patient. Commercial vendors include, e.g., Arthrex (Naples, Fla.). The amount and manner of administration of a preparation of an autologous blood product such as platelet-rich plasma for use in the methods of the present invention may be determined by one of skill in the art without undue experimentation.

As appreciated by one of skill in the art, the methods of the present invention comprise administering the toxins and agents disclosed herein according to any mode and frequency of administration designed by one of skill in the art to achieve the desired inhibitory effects on scar formation and/or stimulatory effects on tissue regeneration over a period of time in a subject in need thereof. Thus, for example, one or more superficial intradermal injections may be administered per day in or near a wound, e.g., every few centimeters in the wound margin partially or completely encompassing the periphery of the wound. The wound may be treated beginning immediately after injury or at any time thereafter up to about 6 months after injury, and for an amount of time until one or more desired prophylactic cosmetic and/or therapeutic effects are obtained. Onset of a treatment regimen, method(s) of administration, frequency of daily administration, length of treatment regimen, etc. can be determined by a skilled practitioner taking into account various factors including, e.g., the concentration and amount of toxin injected, specific botulinum toxin used, type of injury, and the use in combination with of one or more additional agents.

While deep intradermal injections of botulinum toxin have been disclosed in methods to reduce sebum production, botulinum toxin is typically administered in conventional cosmetic procedures by intramuscular injection. The movement of toxin away from the injection site after intramuscular injection has been studied and is characterized in different ways, e.g., "diffusion" (i.e., slow and passive dispersion) or "spread" (i.e. fast and active movement of toxin of toxin away from the desired site of injection. A variety of factors may play a role in these processes, including, e.g., the dosage amount injected, the size of the toxin administered; the rate of dissociation of an injected toxin complex at physiological pH; the size of needle used, whether the formulation of toxin is diluted prior to injection, as well as the technique of the clinician administering the injection. Notwithstanding, as understood by one of skill in the art, after injection, commercial formulations of toxin tend to display minimal diffusion and/or dispersion to non-target tissue. Thus, the administration by injection of botulinum toxin to date has been deemed safe in humans based on the tendency of the injected toxin to remain relatively localized in the target tissue (i.e., muscle tissue) after injection.

Accordingly, diffusion or dispersion of the neurotoxin toxin away from the injection site is also unlikely after intradermal injection. Notwithstanding, it is contemplated herein that the superficial injection of a neurotoxin (or other substance) as a bleb further decreases the likelihood of unwanted movement of the active agent away from the wound site. Specifically, the bleb of toxin can act as a reservoir or depot of toxin in the dermis (evidenced by visible skin blanching) and as such is unlikely to diffuse or spread to underlying, non-target tissue, e.g., the muscle layer. In this manner, the toxin can be delivered and remain in the injection site in an effective concentration. The injection of multiple blebs of small volume (e.g., small aliquots of from about 0.02 to about 0.2 ml/cm$^2$) is also contemplated herein as an additional means of minimizing the possible unwanted diffusion of neurotoxin or other active agent(s) from the wound site while still maintaining a therapeutically effective amount near the wound site.

Neurotoxin and other agents may also be co-administered with a vasoconstrictive agent to reduce the likelihood of unwanted drug dispersion. For example, a vasoconstrictive agent can minimize the spread of the toxin away from the injection site by reducing local blood flow, thus concentrating the toxin at the injection site. The topical and systemic use of such compounds for this purpose, e.g., with local anesthetics, is familiar to one of skill in the art. Vasoconstrictive agents for use herein include, but are not limited to, commercially available formulations of amphetamines, antihistamines, decongestants, and other agents capable of enhancing norepinephrine, epinephrine, or adrenergic activity by stimulating α-adrenergic receptors.

In addition, it is further contemplated herein that toxins and other agents for use in the methods of the instant invention may be formulated for enhanced local activity at the site of the injection in the dermis. Accordingly, the properties of an administered substance may be optimized such that the diffusion and spread of the substance to non-target tissue is minimized. Thus, as contemplated herein, the formulations of toxins or other agents for use with the methods of the instant invention include topical or injectable formulations which exhibit limited diffusion and spread of the toxin or agent away from the site of administration. Such formulations include, e.g., a depot or sustained release injectable formulation. Such long acting formulations also may be administered by implantation in the dermis. A neurotoxin or other agent may be formulated accordingly using suitable polymeric or hydrophobic materials (for instance, in an emulsion with a pharmacologically acceptable oil), with ion exchange resins, or as a sparingly soluble derivative such as, without limitation, a sparingly soluble salt.

Additionally, active compounds for use in the instant invention may be delivered using a sustained-release system, such as semipermeable matrices of solid hydrophobic polymers containing the therapeutic agent. Various sustained-release materials have been established and are well known by those skilled in the art. Sustained-release formulation may, depending on their chemical nature, release the compounds for a few weeks up to over 100 days. Depending on the chemical nature and the biological stability of the therapeutic reagent, additional strategies for protein stabilization may be employed.

Methods of formulating a composition to minimize diffusion in the dermis also may be achieved by one of skill in the art according to conventional methods. For example, the viscosity of the formulation may be adjusted without undue experimentation using conventional pharmaceutical excipients such that possible or potential diffusion of the formulation away from the desired location in vivo is impeded. Accordingly, in addition to the use of bleb reservoirs in superficial intradermal injections, aqueous suspensions for intradermal injection may contain substances which increase the viscosity of the suspension, such as sodium carboxymethyl cellulose, sorbitol, or dextran, pharmaceutically acceptable polymers and/or polymeric gels such as poly (lactic-co-glycolic acid) and like substances familiar to one of skill in the art. Optionally, the suspension may also contain suitable stabilizers and/or agents that increase the solubility of the compounds to allow for the preparation of highly concentrated solutions for intradermal injection.

In another embodiment, a composition comprising a toxin or other agent may be formulated with a drug delivery system to facilitate local administration of the drug at the site of the wound to be treated. Such drug delivery systems are familiar to one of skill in the art and include, for example, liposomes or nanotechnology devices suitable for local, e.g., trans-epidermal drug delivery.

Alternatively, in another embodiment, the toxin or other active agent may be modified according to conventional methods, e.g., pegylated, glycosylated, etc. to optimize the activity of the toxin or other agent intradermally at the site of the injection, e.g., in the wound, and/or in or near the wound margins.

As discussed above, in addition to the physical and chemical properties of the injected product, one of skill in the art familiar with the administration of toxins by injection is aware that the volume and dilution of the administered toxin formulation can also influence the diffusion and spread of the toxin in vivo. Thus, in this regard, it is contemplated herein that a therapeutically effective amount of toxin may be administered in a manner which minimizes the unwanted diffusion and spread of the toxin away from the wound to be treated. Thus, it is contemplated herein that an effective dose of toxin may be injected as several smaller, divided doses if necessary.

In another embodiment, it is contemplated herein that unwanted diffusion of a toxin or other agent for use in the methods of the instant invention may be reduced in vivo by modifying the toxin or agent such that it possesses a chemical or physical predilection for the superficial skin layers at the wound site and not, e.g., for underlying muscle. For example, the toxin or other agent may be linked to a second agent which has specificity to a protein found in the epidermis and/or dermis. Such second agent can be an antibody directed to a target protein found in the dermis and possibly even associated with the wound to be treated, e.g., a protein found in granulation tissue. Similarly, one may administer the drug in a targeted drug delivery system, for example, in a liposome coated with cell-specific antibody. The liposomes will be targeted to and taken up selectively by a cell in the target tissue.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. The disclosure will be further described in the following examples, which are intended to further illustrate certain embodiments of the invention and are not intended to limit the invention in any way.

EXAMPLES

Example 1

A clinical study in healthy human volunteers was conducted to examine the safety and effects of Xeomin® (incobotulinumtoxinA) in the prophylactic treatment of cutaneous wound repair, relative to placebo by administering intradermal injections into the skin in the margins of cutaneous wounds and determining the levels of TGFβ1, 2, and 3 in biopsy samples of wounds treated with Xeomin® and placebo. Clinical improvement of scar cosmesis in several wounds was evaluated by the Principal Investigator and by the subject at day 120. TGFβ1 levels before and after treatment were measured via conventional peroxidase staining of the biopsy samples.

Study Design

A single-center, prospective, double-blind, randomized study of approximately 30 subjects was performed. The subjects were administered superficial intradermal injections of Xeomin® (Merz Pharmaceuticals) on two wounds and placebo on the other two wounds (i.e., administered in the wound margin within 1 cm from the wound) for a total of three times for each wound.

In this "double-blind study" both the patient and the study doctor did not know which wound received the neurotoxin and which received the placebo.

Patients received two biopsies (5 mm/each) in each arm (total of 4 biopsies) to create a wound. Six of the 30 patients were selected to compose a subgroup that received more biopsies (5 mm/each) from the wounded sites at day 7 (Visit 2) and day 120 (Visit 5). Patients not selected to participate in this subgroup did not receive additional biopsies. Photographs from patient's arms were taken to document pretreatment conditions. Unless otherwise indicated, biopsy wounds were treated and bandaged according to conventional methods. Patients were instructed to avoid sun exposure and not to apply any additional product to their wounds during the course of the study.

This study was a double-blind, randomized study. Study participants meeting all inclusion/exclusion criteria were randomly assigned to one of 3 groups:

Group A: two wounds: 2.5 U of Xeomin®/cm2 (total: 30 U/subject) two wounds: placebo (0.05 to 0.2 mls sterile unpreserved 0.9% sodium chloride);

Group B: two wounds: 5 U of Xeomin®/cm2 (total: 60 U/subject) two wounds: placebo (0.05 to 0.2 mls sterile unpreserved 0.9% sodium chloride); and Group C: two wounds: 7.5 U of Xeomin®/cm2 (total: 90 U/subject) two wounds: placebo (0.05 to 0.2 mls sterile unpreserved 0.9% sodium chloride).

Which study drug (Xeomin® or placebo) the patient would receive on each wound was decided by a random assignment; neither the patient nor the treating doctor knew which study drug was being administered.

Commercially available Xeomin® was used in the study. Xeomin® is manufactured, packed and labeled by Merz Pharmaceuticals GmbH, Frankfurt, Germany. Xeomin® has been approved by the US Food and Drug Administration to treat the abnormal head position and neck pain that happens with cervical dystonia in adults, to treat abnormal spasm of the eyelids (blepharospasm) in adults who have had prior treatment with onabotulinumtoxinA (Botox®), and to temporarily improve the look of moderate to severe frown lines between the eyebrows (glabellar lines) in adults. It is currently approved in over 20 countries worldwide for the treatment of abnormal muscular spasms of the neck and around the eyes. More than 84,000 patients have been treated with Xeomin® worldwide since 2005.

The treatment site was cleaned with a chlorhexidine antiseptic solution. Xeomin® (diluted with 0.9% sodium chloride preservative free) or placebo was administered using a thin gauge needle by injecting the material (0.05 to 0.2 ml) into the superficial dermis.

Skin was prepared following standard methodology of cleansing and disinfecting the skin. The skin where the biopsies were taken from was numbed by injecting lidocaine (an anesthetic solution). Two 5 mm punch biopsies were obtained from each arm separated by at least 5 cm from each other.

Treatment

At the Initial Visit tests and procedures were performed on the same day as the study treatment 1 (Visit 1). Two more treatments were given at day 30 (Visit 3), and at day (Visit 4). During this study, one wound on each arm received up to 4 injections of Xeomin® around the wound edges during the treatment. The other wound on each arm received up to 4 injections of placebo around the wound edges during the treatment. The skin was held tightly during injection and small aliquots (0.02 to 0.2 mls) of toxin and diluent (0.9% sodium chloride preservative free) were injected into the superficial dermis, close to the epidermal/dermal junction creating a bleb-liked reservoir of product. The needle was introduced at an angle from 10 to less than 90 degrees visualizing needle placement through the skin to facilitate superficial placement of the toxin. A bleb of product was placed, blanching of the skin and a palpable and visible bump in the skin was observed.

The inner arm was chosen for the biopsy sites due to the distant location of skin to muscle. To reach muscle in this adipose rich area, deep injections would need to be performed placing the needles perpendicular to the skin very deep into the tissue. The biopsies were sutured using standard of care. The subject remained in the study center for 30 minutes after the study injections were completed before being discharged.

Follow-Up Visit 2 (7 Days after the First Treatment):

The following tests and procedures were performed at Visit 2: Patients were asked about how they were feeling and about any medications they had taken or treatments they had received since the last study visit. The wound sutures were removed. Photographs were taken of each wound. The doctor evaluated the appearance of the patients' scars. If the subject was participating in the subgroup study, 2 biopsies were taken from the previously wounded sites (1 biopsy/wound) per side (left-right arm).

Follow-Up Visits 3 and 4 (30 Days after the First Treatment and 60 Days after First Treatment):

The following tests and procedures were performed at Follow-Up Visits 3 and 4: Patients were asked about how they were feeling and about any medications they had taken or treatments they had received since the last study visit. The doctor evaluated the patients' scars appearance. A new treatment was performed, i.e., toxin was injected again, same as during the first treatment visit.

Follow-Up Visit 5 (120 Days after the First Treatment):

The following tests and procedures were performed at Follow-Up Visit 5: Patients were asked about how they were feeling and about any medications they had taken or treatments they had received since the last study visit. Photographs were taken of each wound. Patients were asked to evaluate their scar appearance. The doctor evaluated the patients' scars appearance. If the subject was participating in the subgroup study, 2 biopsies were taken from the wounded sites (1 biopsy/wound) of the wounds that were not previously re-biopsied.

Results

Biopsy tissue from 7 volunteers were processed and analyzed by a blinded dermatologist evaluator who is an expert in the field of skin pathology at the Institute of Anti-Aging Research (Virginia Beach, Va.). Biopsies were obtained at day 7 and day 120, after initial wounding. Treatment was performed immediately after wounding, at day 30 and at day 60 (only on remaining wounds). The levels of expression of TGFβ1 were measured using immunoperoxidase staining of the samples collected by punch biopsy at days 7 and 120 after the first treatment. It was expected that placebo samples should exhibit more intradermal staining than samples treated with botulinum toxin A if botulinum toxin A could inhibit TGFβ1 in vivo after a superficial intradermal injection that did not result in muscular paralysis; the extent of any potential inhibitory effect, let alone effects of the toxin on wound healing in the absence of concomitant muscular paralysis, were unknown. The preliminary results are provided in Table 1.

TABLE 1

Summary of Preliminary Results

| Subject | Day 7 | Day 120 | Comments |
|---|---|---|---|
| 1 (Right-BTXA; Left-placebo) | Left side has more staining PLACEBO | Left side has more staining PLACEBO | Both days matched with treatment code |
| 3 (Right-placebo; left-BTXA) | Both sides have approximately equal staining | Right side has more staining PLACEBO | Day 120 matched with treatment code |
| 4 (Right-BTXA; Left-Placebo) | Right side has more staining | Left side has more staining PLACEBO | Day 120 matched with treatment code |
| 5 (Right-placebo; Left-BTXA) | Right side has more staining PLACEBO | Right side has more staining PLACEBO | Both days matched with treatment code |
| 6 (Right-BTXA; Left-Placebo) | Left side has more staining PLACEBO | Left side has more staining PLACEBO | Both days matched with treatment code |
| 7 (Right-BTXA; Left-placebo) | Both sides have approximately equal staining | Right side has more staining | No matched day |

Day 7 tissue samples were difficult to process due to skin being still fragile since it was still healing.

FIG. 1 shows the appearance of scars from wounds treated with botulinum toxin A (left) and with placebo (right) 120 days earlier for Subject 3.

FIG. 2 shows a 3-dimensional (3-D) image 120 days post-wounding for Subject 3 of the distal left wound, treated with botulinum toxin A. In comparison, FIG. 3 shows a 3-D image 120 days post-wounding for Subject 3 of the distal right wound, treated with Placebo. The 3-D image of the left wound, treated with BTX-A has a smaller elevation than the right wound, treated with placebo.

FIG. 4 shows histology samples stained with peroxidase 120 days after wounding for Subject 3. The dermis of right section, treated with placebo, has more stained TGFβ1 and more collagen structured as bundles (such as found in a scar) compared with the left specimen which was treated with botulinum toxin A in which the collagen fibers are more randomly arranged, more consistent with uninjured tissue. Specifically, the treated tissue shows the formation of rete-ridges and collagen deposition in the wound that more closely resembles that seen in uninjured tissue.

FIG. 5 shows the appearance of scars from wounds treated with botulinum toxin A (right) and with placebo (left) 120 days earlier for Subject 6. The treated tissue shows the formation of rete-ridges and collagen deposition in the wound that more closely resembles that seen in uninjured tissue.

FIG. 6 shows histology samples stained with peroxidase 120 days after wounding for Subject 6. The dermis of left section, treated with placebo, has more stained TGFβ1 and collagen structured as bundles (scar) compared with the right, treated with botulinum toxin A in which the collagen fibers are more randomly arranged. In addition, the epidermis on the left does not have the irregular rete ridges of normal wound healing epidermis found on the right. Specifically, the treated tissue shows the formation of rete-ridges and/or collagen deposition in the wound that more closely resembles that seen in uninjured tissue.

Follow up Analysis: Of 11 medical professionals who have evaluated the lesions approximately 20 months after initial injury and treatment, 11 out of 11 (100%) agreed that the wounds treated with the active compound had a better cosmetic result by look and feel compared to the placebo.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of decreasing scar formation in a skin wound in a subject in need thereof comprising:
   administering a superficial intradermal injection to said subject in or near said wound, wherein the injection comprises an effective amount of a neurotoxin and wherein the injection forms a superficial intradermal bleb reservoir of neurotoxin in the dermis of the subject in or near the wound site,
   wherein the amount is sufficient to decrease formation of scar tissue and does not cause paralysis of musculature surrounding the wound,
   wherein the neurotoxin is botulinum neurotoxin or a derivative thereof.

2. The method of claim 1 wherein the botulinum neurotoxin is selected from the group consisting of botulinum neurotoxin A, B, C, D, E, F, and G.

3. The method of claim 1 wherein said method further comprises administering one or more agents in addition to the neurotoxin in or near said wound.

4. The method of claim 3 wherein said agent is administered prior to administration of said neurotoxin, after administration of said neurotoxin, and/or concurrently with the administration of said neurotoxin.

5. The method of claim 1 wherein the neurotoxin is diluted prior to injection.

6. The method of claim 5 wherein one or more aliquots of the diluted neurotoxin are injected into the superficial dermis or epidermal/dermal junction near the wound site creating one or more superficial intradermal bleb reservoirs of neurotoxin.

7. The method of claim 6 wherein said aliquots of the diluted neurotoxin are injected in the amount of from about 0.02 ml per cm$^2$ to about 0.2 ml per cm$^2$ per injection.

8. The method of claim 1 wherein further one or more superficial intradermal injections are performed in the wound itself and/or in or near the wound site.

9. The method of claim 8 wherein the injections are made in the wound margin from about 0 cm to about 5 cm from the wound.

10. The method of claim 9 wherein the injections are made in the wound margin within about 3 cm from the wound.

11. The method of claim 8 wherein the injections are made around the entire wound site, or in one or more sections thereof.

12. The method of claim 3 wherein said agent is selected from the group consisting of anesthetics, antimicrobials, and vasoconstrictive agents.

13. The method of claim 12 wherein the vasoconstrictive agent is selected from the group consisting of amphetamines, antihistamines, decongestants, and other agents capable of enhancing norepinephrine, epinephrine, or adrenergic activity by stimulating α-adrenergic receptors.

14. The method of claim 12, wherein said anesthetic is selected from the group consisting of lidocaine, bupivacaine, and mepivacaine.

15. The method of claim 3 wherein said agent is an agent capable of enhancing skin repair, skin regeneration and/or wound healing.

16. The method of claim 15 wherein the agent can inhibit expression and/or activity of a growth factor or a cytokine.

17. The method of claim 16 wherein the agent can inhibit the expression and/or activity of one or more proteins selected from the group consisting of homeobox proteins, early growth protein 1, vascular endothelial growth factor, insulin-like growth factor, integrins, canonical Wnt proteins, connexin 43, and TGFβ.

18. The method of claim 15 wherein said agent is one or more autologous blood product.

19. The method of claim 18 wherein said autologous blood product is a minimally altered autologous blood product.

20. The method of claim 19 wherein said minimally altered autologous blood product is selected from the group consisting of interleukins, platelet derived growth factors, and connective tissue growth factor.

21. The method of claim 15 wherein said agent is platelet-rich plasma.

22. The method of claim 1 wherein the neurotoxin and/or the agent are modified, formulated, and/or administered to optimize the activity of the neurotoxin and/or the agent in the superficial layers of the skin in or near the site of the wound, including at the wound margins.

23. The method of claim 1 wherein the neurotoxin and/or the agent are modified, formulated and/or administered in a manner designed to minimize diffusion and/or dispersion of the neurotoxin or additional agent away from the site of administration.

* * * * *